United States Patent [19]

Takaya et al.

[11] Patent Number: 4,725,600
[45] Date of Patent: Feb. 16, 1988

[54] PYRIMIDINE COMPOUNDS HAVING ACTIVITY AS A CARDIOTONIC ANTI-HYPERTENSIVE CEREBROVASCULAR VASODILATOR AND ANTI-PLATELET AGGREGATION AGENT

[75] Inventors: Takao Takaya, Kawanishi; Masayoshi Murata, Osaka; Kiyotaka Ito, Ibaragi, all of Japan

[73] Assignee: Fujisawa Pharmaceutical Co., Ltd., Osaka, Japan

[21] Appl. No.: 751,867

[22] Filed: Jul. 5, 1985

[30] Foreign Application Priority Data

Jul. 13, 1984 [GB] United Kingdom ............... 8417852
Sep. 19, 1984 [GB] United Kingdom ............... 8423667
Dec. 3, 1984 [GB] United Kingdom ............... 8430456

[51] Int. Cl.[4] ............... A61K 31/495; C07D 403/04; C07D 239/24
[52] U.S. Cl. ................... 514/269; 514/252; 514/254; 514/258; 514/272; 514/274; 544/263; 544/295; 544/315; 544/316; 544/317; 544/318; 544/319; 544/320; 544/322; 544/323; 544/324; 544/325; 544/326
[58] Field of Search ............... 544/326, 295, 263, 315, 544/316, 317, 318, 319, 320, 322, 323, 324, 325; 514/256, 254, 252, 258, 272, 274, 269

[56] References Cited

U.S. PATENT DOCUMENTS 3,707,560 12/1972 De Angelis et al. ............... 544/326
3,859,288 1/1975 De Angelis et al. ............... 544/326
3,908,012 9/1975 De Angelis et al. ............... 544/326
3,950,525 4/1976 De Angelis et al. ............... 544/326
4,450,162 5/1984 Kamioka et al. ................... 544/326

OTHER PUBLICATIONS

Brown et al., *Chemical Abstracts*, vol. 74:75908p, 1971.
Ursprung et al., *Chemical Abstracts*, vol. 70:115172v, 1969.

*Primary Examiner*—Donald G. Daus
*Assistant Examiner*—Cecilia Shen
*Attorney, Agent, or Firm*—Oblon, Fisher, Spivak, McClelland & Maier

[57] ABSTRACT

The invention relates to pyrimidine compounds of the formula:

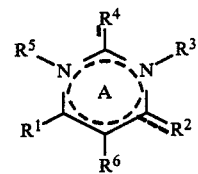

wherein the substituents $R^1$, $R^2$, $R^3$, $R^4$, $R^5$ and $R^6$ are as herein defined, having activity as a cardiotonic, antihypertensive, cerebrovascular vasodilator and antiplatelet aggregation agent.

18 Claims, No Drawings

PYRIMIDINE COMPOUNDS HAVING ACTIVITY AS A CARDIOTONIC ANTI-HYPERTENSIVE CEREBROVASCULAR VASODILATOR AND ANTI-PLATELET AGGREGATION AGENT

This invention relates to new pyrimidine derivatives. More particularly, this invention relates to new pyrimidine derivatives and pharmaceutically acceptable salts thereof which have pharmacological activities, processes for preparation thereof, a pharmaceutical composition comprising the same and method of use thereof.

Accordingly, one object of this invention is to provide the pyrimidine derivatives and pharmaceutically acceptable salt thereof.

Another object of this invention is to provide processes for preparation of the pyrimidine derivatives and pharmaceutically acceptable salts thereof.

A further object of this invention is to provide a pharmaceutical composition comprising said pyrimidine derivative or pharmaceutically acceptable salt thereof as a cardiotonic agent, antihypertensive agent, cerebrovascular vasodilator and anti-platelet agent and/or anti-allergic agent.

Still further object of this invention is to provide a method of using said pyrimidine derivative or a pharmaceutically acceptable salt thereof for therapeutic treatment of heart disease, hypertension, cerebrovascular disease and thrombosis of human being and animals.

Some pyrimidine derivatives having antihypertensive and vasodilative activities have been known as described, for examples, in European Patent Publication No. 0010759.

The pyrimidine derivatives of this invention are novel and represented by the following general formula [I]:

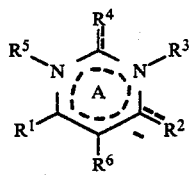

wherein $R^1$ is hydrogen, aryl optionally having substituent(s) selected from lower alkoxy, lower alkyl, halogen and lower alkylthio or

in which

is a N-containing heterocyclic group;
$R^2$ is (a) =N—$R_a^2$ or

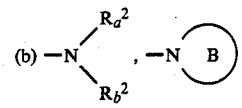

or —O—$R_a^2$
in which
$R_a^2$ is aryl optionally substituted with lower alkyl, lower alkoxy, amino and/or acylamino,
$R_b^2$ is hydrogen or lower alkyl,
—NB is a N-containing heterocyclic group optionally substituted with acyl and/or ar(lower)alkyl;
$R^3$ is hydrogen, lower alkyl or no significance;
$R^4$ is (a) imino optionally substituted with lower alkyl, aryl or ar(lower)alkyl, or (b) lower alkyl, hydrogen, halogen, lower alkylthio, amino optionally substituted with lower alkyl, aryl, ar(lower)alkyl and/or acyl, —NC or hydrazino optionally substituted with acyl, in which —NC is a N-containing heterocyclic group optionally substituted with acyl and/or ar(lower)alkyl;
$R^5$ is hydrogen, lower alkyl, lower alkanoyl optionally substituted with lower alkylamino or no significance; or
$R^3$ and $R^4$, or $R^4$ and $R^5$ are taken together with the adjacent nitrogen atom and carbon atom to form a N-containing heterocyclic ring;
$R^6$ is hydrogen, lower alkyl, halogen or aryl optionally having substituent(s) selected from lower alkoxy, lower alkyl, halogen and lower alkylthio substituents;
the ═ bond represents single bond or double bond; and the dotted line in the ring A represents one, two or three additional C—C and/or C—N bond(s) in the ring system, provided that $R^1$ and $R^6$ are not both hydrogen;

As to the object compound [I], the following points are to be noted. That is, when $R^3$ and/or $R^5$ are hydrogen, then the pyrimidine moiety in the object compound [I] can be alternatively represented by its tautomers.

For example, when both of $R^3$ and $R^5$ are hydrogen, $R^4$ is lower alkyl and $R^2$ is =N—$R_a^2$, the compound [I] can be represented by one of the structural formula (A) to (C) as shown in the following.

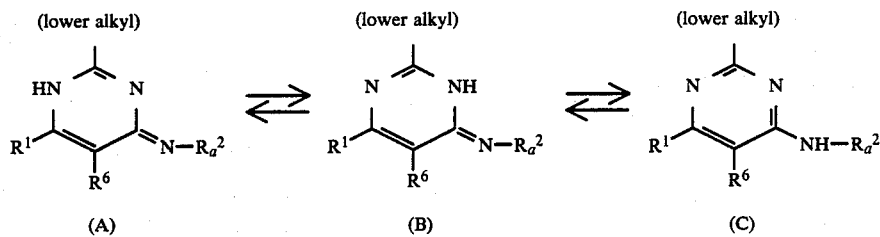

wherein $R^1$, $R_a^2$, and $R^6$ are each as defined above.

The object compound may be presented in any of these tautomeric forms and may co-exist in an equilibrium mixture. Accordingly all of these tautomeric forms are included within the scope of the present invention.

The object compound [I] and their salts of the present invention can be prepared by the following processes.

Process 1

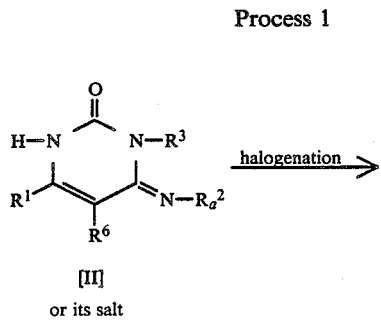

[II]
or its salt halogenation →

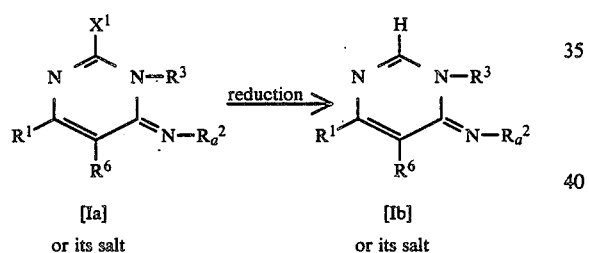

[Ia]
or its salt

Process 2

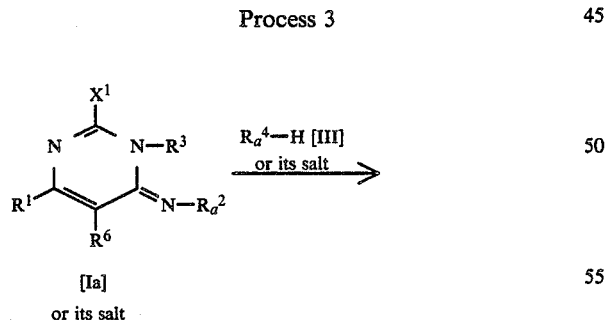

[Ia]         [Ib]
or its salt  or its salt

Process 3

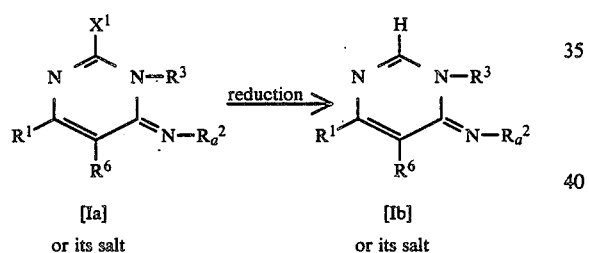

[Ia]
or its salt $R_a^4$—H [III] or its salt →

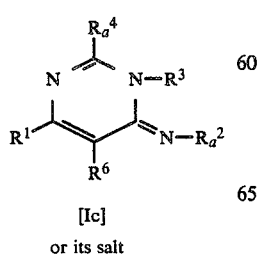

[Ic]
or its salt

Process 4

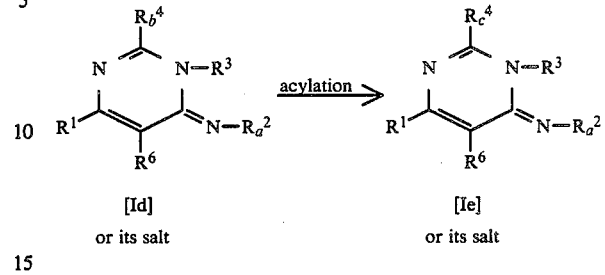

[Id]                    [Ie]
or its salt             or its salt acylation →

Process 5

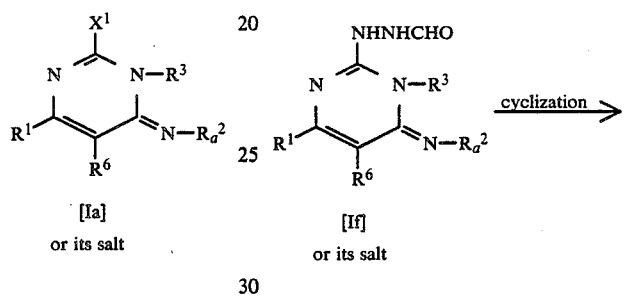

[If]
or its salt cyclization →

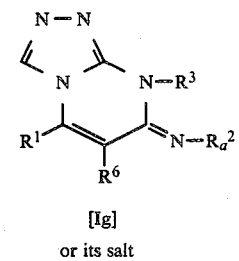

[Ig]
or its salt

Process 6

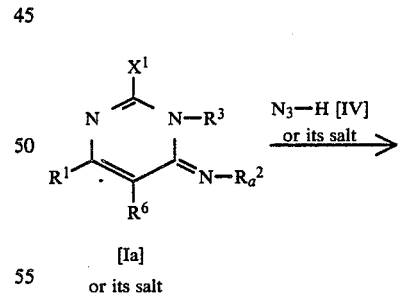

[Ia]
or its salt $N_3$—H [IV] or its salt →

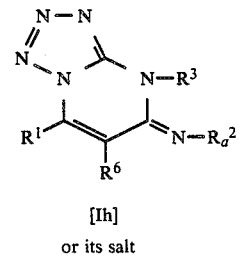

[Ih]
or its salt

Process 7

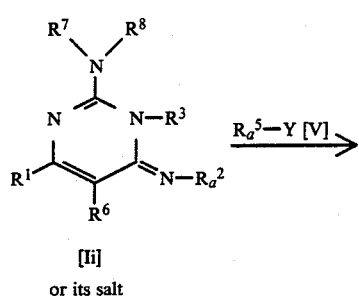 $\xrightarrow{R_a^5-Y\ [V]}$ 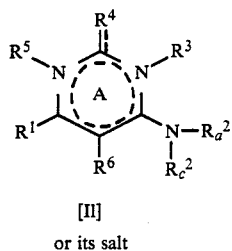

[Ii]
or its salt

[Ij]
or its salt

Process 8

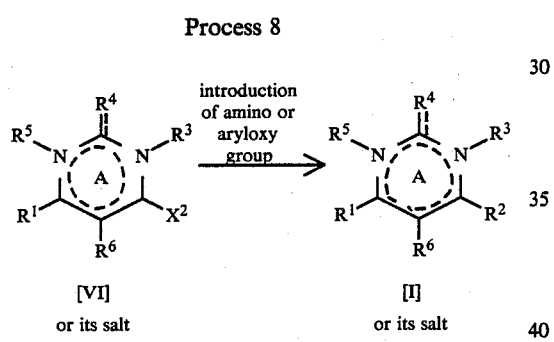

[VI]
or its salt

[I]
or its salt

Process 9

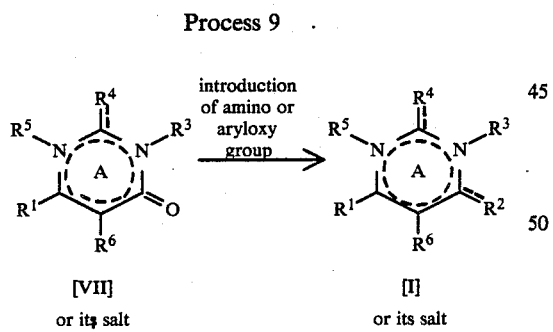

[VII]
or its salt

[I]
or its salt

Process 10

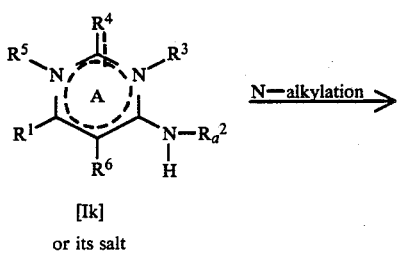 $\xrightarrow{N-\text{alkylation}}$

[Ik]
or its salt

[II]
or its salt

Process 11

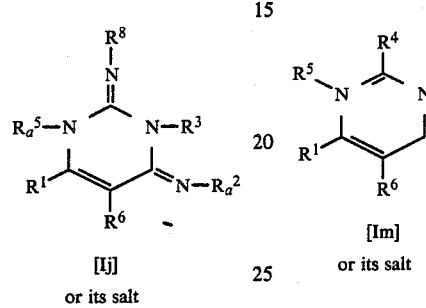 $\xrightarrow{\text{reduction}}$

[Im]
or its salt

[In]
or its salt

Process 12

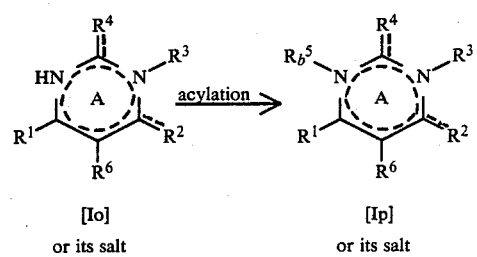 $\xrightarrow{\text{acylation}}$

[Io]
or its salt

[Ip]
or its salt

Process 13

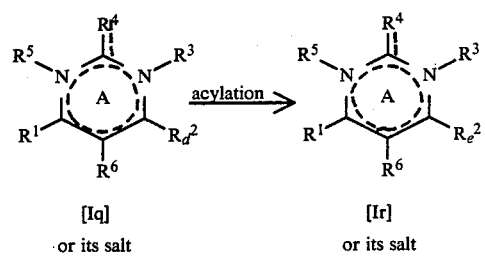 $\xrightarrow{\text{acylation}}$

[Iq]
or its salt

[Ir]
or its salt wherein
$R^1$, $R^2$, $R^3$, $R^4$, $R^5$, $R^6$, $R_a^2$, $=$ bond and the dotted line in the ring A are each as defined above;
$X^1$ and $X^2$ are each halogen;
$R_c^2$ is lower alkyl;
$R_d^2$ is piperazin-1-yl or arylamino substituted with amino;
$R_e^2$ is piperazin-1-yl substituted with acyl or arylamino substituted with acylamino,
$R_a^4$ is lower alkylthio or amino optionally substituted with lower alkyl, aryl, ar(lower)alkyl and/or acyl, $-N\underset{}{\bigcirc}$ (in which $-N\underset{}{\bigcirc}$ is as defined above), or hydrazino optionally substituted with acyl;
$R_b^4$ is piperazin-1-yl, hydrazino or amino, $R_c^4$ is piperazin-1-yl substituted with acyl, hydrazino substituted with acyl or acylamino;

$R_a^5$ is lower alkyl;

$R_b^5$ is lower alkanoyl optionally substituted with lower alkylamino;

$R^7$ is lower alkyl;

$R^8$ is lower alkyl, aryl or ar(lower)alkyl; and

Y is a leaving group.

In the above and subsequent description of the present specification, suitable examples of the various definitions to be included within the scope of the invention are explained in detail in the following.

The term "lower" is intended to mean 1 to 6 carbon atom(s) unless otherwise indicated.

Suitable examples of "lower alkyl" may be a straight or branched one such as methyl, ethyl, propyl, isopropyl, butyl, isobutyl, tert-butyl, pentyl, hexyl or the like.

Suitable examples of "aryl" may be phenyl, naphthyl or the like.

The aryl group for $R^1$ and $R^6$ may have 1 to 4, preferably 1 to 3 substituent(s) selected from lower alkoxy [e.g. methoxy, ethoxy, propoxy, isopropoxy, butoxy, tert-butoxy, pentyloxy, hexyloxy, etc.], the abovementioned lower alkyl group, halogen [e.g. fluorine, chlorine, bromine and iodine] and lower alkylthio [e.g. methylthio, ethylthio, propylthio, isopropylthio, hexylthio, etc.]. Preferable examples of the aryl group having such substituent(s) may be lower alkoxy substituted aryl [e.g. 4-methoxyphenyl, 3,4-dimethoxyphenyl, 3,4,5-trimethoxyphenyl, 2,3,4-trimethoxyphenyl, 2-ethoxyphenyl, 4-hexyloxyphenyl, etc.], lower alkyl substituted aryl [e.g. p-tolyl, m-tolyl, o-tolyl, 4-ethylphenyl, 4-hexylphenyl, 2,6-dimethylphenyl, 3,4-dimethylphenyl, 2,4,6-trimethylphenyl, etc.], lower alkoxy and lower alkyl substituted aryl [e.g. 2-methyl-4-methoxyphenyl, 2-ethyl-4-methoxyphenyl, 3-ethyl-4-ethoxyphenyl, etc.], halogenated aryl [e.g. 4-fluorophenyl, 3-fluorophenyl, 4-chlorophenyl, 4-bromophenyl, 4-iodophenyl, 3,4-difluorophenyl, etc.], lower alkylthio substituted aryl [e.g. 4-methylthiophenyl, 4-ethylthiophenyl, 2propylthiophenyl, 4-hexylthiophenyl, etc.], lower alkylthio and lower alkoxy substituted aryl [e.g. 3-methoxy-4-methylthiophenyl, 4-methoxy-2-methylthiophenyl, 3-methoxy-4-ethylthiophenyl, 2-ethoxy-4-hexylthiophenyl, etc.] or the like.

The aryl group for $R_a^2$ may be substituted with lower alkyl, lower alkoxy, amino and/or acylamino, for example, lower alkanesulfonylamino [e.g., mesylamino, ethanesulfonylamino, isobutanesulfonylamino, etc.]. Suitable examples of the aryl group for $R_a^2$ having such substituent(s) can be referred to those as exemplified for the aryl group for $R^1$ and $R^6$ in the above and 3-aminophenyl, 4-aminophenyl, 3-mesylaminophenyl, 4-mesylaminophenyl, 4-ethanesulfonylaminophenyl or the like.

Suitable examples of "arylamino substituted with amino group" for $R_d^2$ may be 4-aminoanilino, 3-aminoanilino or the like.

Suitable examples of "arylamino substituted with acylamino group" for $R_e^2$ may be 2-mesylaminoanilino, 4-mesylaminoanilino, 4-ethanesulfonylaminoanilino, 4-isopropanesulfonylaminoanilino or the like.

Suitable examples of "ar(lower)alkyl" may be benzyl, phenethyl, 3-phenylpropyl, benzhydryl, trityl or the like.

Suitable examples of the "N-containing heterocyclic group" may include unsaturated 5 or 6 membered heteromonocyclic group containing 1 to 4 nitrogen atom(s), for example, pyrrolyl, pyrrolinyl, imidazolyl, pyrazolyl, pyridyl, 1,2,3,6-tetrahydropyridyl, 1,2-dihydropyridyl, pyrimidinyl, pyrazinyl, pyridazinyl, triazolyl, tetrazolyl, etc.;

saturated 5 or 6 membered heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 5 nitrogen atom(s), for example, indolyl, isoindolyl, indolinyl, benzimidazolyl, quinolyl, benzotriazolyl, etc.; and the like.

Preferable N-containing heterocyclic group for

is 5 or 6 membered heteromonocyclic group containing 1 to 4 nitrogen atom(s), and which includes 4-pyridyl, 3-pyridyl, 1,2,3,6-tetrahydropyridin-1-yl or the like.

The N-containing heterocyclic group for —N(B) and —N(C) may be substituted with acyl such as lower alkanoyl [e.g. formyl, acetyl, propionyl, valeryl, pivaloyl, etc.], aroyl optionally substituted with suitable substituent(s) selected from halogen, sulfamoyl, lower alkyl and lower alkanesulfonylamino [e.g. benzoyl, p-toluoyl, 4-fluorobenzoyl, 4-chlorobenzoyl, 2,4-difluorobenzoyl, 4-chloro-3-sulfamoylbenzoyl, 4-trifluoromethyl-3-sulfamoylbenzoyl, 2,4-dichloro-5-sulfamoylbenzoyl, etc.] or the like, and/or with ar(lower)alkyl such as benzyl, 2-phenethyl, 2-phenylpropyl, benzhydryl or the like.

Preferable example of the N-containing heterocyclic group for —N(B) and —N(C) having acyl and/or ar(lower)alkyl group may be 4-formylpiperazin-1-yl, 4-acetylpiperazin-1-yl, 4-benzoylpiperazin-1-yl, 4-(4-fluorobenzoyl)piperazin-1-yl, 1-acetylimidazolidin-2-yl, 4-(2,4-dichloro-5-sulfamoylbenzoyl)piperazin-1-yl, 4-(4-trifluoromethyl-3-sulfamoylbenzoyl)piperazin-1-yl, 4-benzylpiperazin-1-yl, 4-benzhydrylpiperazin-1-yl, 4-(2-chloro-4-benzhydryl-5-sulfamoyl)piperazin-1-yl or the like.

The N-containing heterocyclic ring formed by $R^3$ and $R^4$ or $R^4$ and $R^5$ with the adjacent nitrogen atom and carbon atom may be the one corresponding to the N— containing heterocyclic group as exemplified in the above.

The "piperazin-1-yl substituted with acryl" for $R_e^2$ and $R_c^4$ is piperazin-1-yl group substituted with acyl group as exemplified before and suitable examples thereof are 4-formylpiperazin-1-yl, 4-acetylpiperazin-1-yl, 4-benzoylpiperazin-1-yl, 4-(2,4-dichloro-5-sulfamoylbenzoyl)piperazin-1-yl, 4-(4-trifluoromethyl-3-sulfamoylbenzoyl)piperazin-1-yl, 4-(4-fluorobenzoyl)-piperazin-1-yl or the like.

The suitable acylamino group may be lower alkanesulfonylamino group such as mesylamino, ethanesulfonylamino, propanesulfonylamino, isopentanesulfonylamino, butanesulfonylamino or the like.

The imino group for $R^4$ may be substituted with the aforementioned lower alkyl group, aryl group or ar(lower)alkyl group. Preferable examples of the imino group having such a substituent may be lower alkyl substituted imino [e.g. methylimino, ethylimino, hexylimino, etc.], aryl substituted imino [e.g. phenylimino, naphthylimino, etc.], ar(lower)alkyl substituted imino [e.g. benzylimino, phenethylimino, benzhydrylimino, etc.], or the like.

Suitable examples of "halogen" may include chlorine, bromine iodine and fluorine.

Suitable examples of "lower alkylthio" may be methylthio, ethylthio, propylthio, isopropylthio, butylthio, penthylthio, hexylthio or the like.

The amino group for $R^4$ and $R_a^4$ may have substituent(s) selected from the lower alkyl group, aryl group ar(lower)alkyl group and acyl, for example, lower alkanesulfonyl group as exemplified before. Preferable examples of the amino group having such substituent(s) may be lower alkyl substituted amino [e.g. methylamino, ethylamino, propylamino, isopropylamino, hexylamino, dimethylamino, diethylamino, dipropylamino, N-ethyl-N-methylamino, N-methyl-N-propylamino, etc.], aryl substituted amino [e.g. anilino, diphenylamino, naphthylamino, etc.], ar(lower)alkyl substituted amino [e.g. benzylamino, phenethylamino, tritylamino, dibenzylamino, etc.], lower alkyl and aryl substituted amino [e.g. N-methylanilino, N-ethylanilino, etc.], lower alkyl and ar(lower)alkyl substituted amino [e.g. N-benzyl-N-methylamino, N-phenethyl-N-methylamino, etc.] and lower alkanesulfonylamino as defined above.

The hydrazino group for $R^4$, $R_a^4$ and $R_c^4$ may be substituted with acyl as mentioned above.

Preferable examples of the hydrazino having an acyl group may be 2-formylhydrazino, 2-acetylhydrazino, 2-propionylhydrazino, 2-benzoylhydrazino, 2-(4-fluorobenzoyl)hydrazino or the like.

Suitable examples of "lower alkanoyl" may include formyl, acetyl, propionyl, valeryl, pivaloyl or the like.

The "lower alkanoyl" group for $R^5$ and $R_b^5$ may be substituted with lower alkylamino such as methylamino, ethylamino, 1-ethylamino, propylamino, butylamino or the like. Preferable examples of "lower alkanoyl substituted with lower alkylamino" may be methylaminoacetyl, methylcarbamoyl, ethylcarbamoyl or the like.

The ring A containing one, two or three additional C—C and/or C—N bond(s) represented by the dotted lines may include pyrimidine, 3,4-dihydropyrimidine, 1,2,3,4-tetrahydropyrimidine and the like.

More specifically, the pyrimidine derivatives [I] of this invention may include the compounds illustrated in the following formulae, their salts and their tautomers.

[I-1]

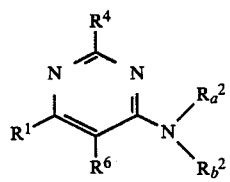

[I-2]

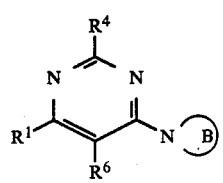

[I-3]

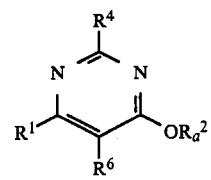

[I-4]

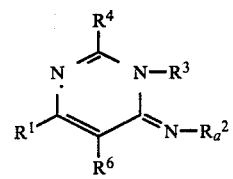

[I-5]

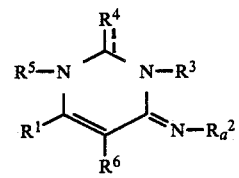

[I-6]

wherein all symbols are each as defined above.

Suitable examples of the leaving group for Y may be halide [e.g. chloride, bromide and iodide], sulfonate [e.g. benzenesulfonate, p-toluenesulfonate, methanesulfonate, etc.], or the like.

Suitable pharmaceutically acceptable salts of the object compounds [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, glutamic acid salt, ornithine salt, etc.], and the like.

In this respect, it is to be noted that the compounds [Ia] to [Ir] are included within the scope of the compound [I], and accordingly the suitable salts of these compounds [Ia] to [Ir] are to be referred to those as exemplified for the object compound [I] in the above.

The processes for preparing the object compound [I] and salt thereof are explained in detail in the following.

Process 1

The object compound [Ia] and its salt can be prepared by halogenating a compound [II] or its salt.

Suitable salts of the compound [II] may be the same as those exemplified for the compound [I].

Suitable examples of the halogenating agent to be used in this process may include a conventional ones such as phosphorus oxyhalide [e.g. a phosphorus oxybromide, phosphorus oxychloride, etc.], phosphorus pentahalide [e.g. phosphorus pentabromide, phosphorus pentachloride, phosphorus pentafluoride, etc.], phosphorus trihalide [e.g. phosphorus tribromide, phosphorus trichloride, phosphorus trifluoride, etc.], thionyl halide [e.g. thionyl chloride, thionyl bromide, etc.], triphenylphosphine dihalide [e.g. triphenylphosphine dichloride, triphenylphosphine dibromide, etc.], or the like.

This reaction is usually carried out in a conventional solvent such as methylene chloride, chloroform, carbon tetrachloride, benzene, tetrahydrofuran, dimethylformamide, dimethyl sulfoxide or any other organic solvent which does not adversely influence the reaction. In case that the halogenating agent is liquid, it can be used as a solvent.

The reaction temperature is not critical, and the reaction can be carried out under cooling to heating.

Process 2

The object compound [Ib] and its salt can be prepared by reducing a compound [Ia] or its salt.

The reaction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], tin hydride compound [e.g. triphenyltin hydride, tributyltin hydride, dibutyltin hydride, etc.], sodium borohydride, aluminum borohydride, or the like; a combination of an alkali metal [e.g. lithium, sodium, potassium, etc.] and alcohol [e.g. methanol, ethanol, t-butyl alcohol, etc.]; a combination of an alkaline earth metal [e.g. magnesium, calcium, etc.] and alcohol [e.g. methanol, ethanol, amyl alcohol, etc.]; a combination of zinc and an acid [e.g. acetic acid, propionic acid, hydrochloric acid, etc.]; or the like.

Suitable catalysts to be used in the catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction of this process is usually carried out in a conventional solvent such as water, alcohol [e.g. methanol, ethanol, propanol, etc.], diethyl ether, dioxane, tetrahydrofuran, acetic acid, propionic acid or the like. These solvents are selected according to the kinds of the reduction method, reducing agents or catalysts to be used in this process.

The reaction temperature is not critical, and the reaction can be carried out under cooling to heating.

Process 3

The object compound [Ic] and its salt can be prepared by reacting a compound [Ia] or its salt with a compound [III] or its salt.

Suitable salts of the compound [III] except the lower alkanethiol may be the same as those exemplified for the compound [I], and the suitable salts of the thiol compound [III] may be a conventional base addition salt such as an inorganic base salt [e.g. lithium salt, sodium salt, potassium salt, calcium salt, barium salt, etc.], an ammonium salt, an organic salt [e.g. pyridine salt, triethylamine salt, etc.], or the like.

This reaction is preferably conducted in the presence of an inorganic base such as an alkali metal hydride [e.g. sodium hydride, potassium hydride, etc.], an alkaline earth metal hydride [e.g. calcium hydride, magnesium hydride, etc.], an alkali metal hydroxide [e.g. sodium hydroxide, potassium hydroxide, etc.], an alkali metal carbonate or bicarbonate [e.g. sodium carbonate, potassium carbonate, sodium bicarbonate, potassium bicarbonate, etc.], or the like.

This reaction is usually carried out in a conventional solvent such as water, methanol, ethanol, propanol, dioxane, tetrahydrofuran, dimethylformamide, methylene chloride, chloroform or any other organic solvent which does not adversely influence the reaction.

The reaction temperature is not critical, and the reaction can be carried out under cooling to heating.

Process 4

The object compound [Ie] and its salt can be prepared by acylating a compound [Id] or its salt.

Suitable examples of the acylating agent to be used in this process may be an organic acid such as lower alkanoic acid [e.g. formic acid, acetic acid, propionic acid, valeric acid, etc.], arylcarboxylic acid [e.g. benzoic acid, naphthoic acid, 4-fluorobenzoic acid, 4-chlorobenzoic acid, 4-chloro-3-sulfamoylbenzoic acid, 2,4-dichloro-5-sulfamoylbenzoic acid, etc.], lower alkanesulfonic acid, isocyanate [e.g. methylisocyanate, ethylisocyanate etc.]; a salt thereof or a reactive derivative at the carboxy group or sulfo group thereof.

Suitable salts of the acid may be a conventional base salt such as inorganic base salt [e.g. sodium salt, potassium salt, calcium salt, magnesium salt, etc.], organic base salt [e.g. trimethylamine salt, triethylamine salt, pyridine salt, etc.], or the like.

Suitable examples of the reactive derivative at the carboxy group or sulfo group may be an acid halide [e.g. acid chloride, acid bromide, sulfonyl chloride, sulfonyl bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower-)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

This reaction is usually carried out in a conventional solvent such as water, methanol, ethanol, propanol, tetralin, tetrahydrofuran, dioxane, chloroform, toluene, dimethylformamide, dimethylsulfoxide or any other organic solvent which does not adversely influence the reaction.

This reaction is preferably conducted in the presence of a conventional base such as an inorganic base exemplified in Process 3 or an organic base [e.g. trimethylamine, triethylamine, pyridine, etc.].

In case that the acylating agent is a free acid or its salt, the reaction is preferably conducted in the presence of a conventional condensing agent [e.g. N,N'-dicyclohexylcarbodiimide, etc.].

The reaction temperature is not critical, and the reaction can be carried out under cooling to heating.

Process 5

The object compound [Ig] and its salt can be prepared by cyclizing a compound [If] or its salt.

This reaction is carried out in the absence or presence of a conventional solvent such as water, methanol, ethanol, propanol, tetralin, tetrahydrofuran, dioxane, chloroform, toluene, dimethylformamide, dimethylsulfoxide or any other organic solvent which does not adversely influence the reaction.

This reaction is preferably carried out in the presence of an acid such as an organic acid [e.g. formic acid, acetic acid, benzenesulfonic acid, p-toluenesulfonic acid, trifluoroacetic acid, etc.], an inorganic acid [e.g. hydrochloric acid, hydrobromic acid, sulfuric acid, etc.], a cationic exchange resin (acid type) [e.g. sulfonate polystyrene resin, etc.], or the like.

The reaction can also be conducted preferably under dehydrating conditions such as an azeotropic dehydration, in the presence of a dehydrating agent or the like.

Suitable examples of the dehydrating agent may be phosphorus compound [e.g. polyphosphoric acid, polyphosphoric acid ester, phosphorus oxychloride, phosphorus oxybromide, phosphorus pentoxide, etc.], acid anhydride [e.g. acetic anhydride, benzoic anhydride, etc.], or the like.

The reaction temperature is not critical, and the reaction is usually carried out at ambient temperature or under warming or heating.

Process 6

The object compound [Ih] and its salt can be prepared by reacting a compound [Ia] or its salt with a compound [IV] or its salt.

Suitable salts of the compound [IV] may be a conventional base addition salt such as an inorganic base salt [e.g. lithium salt, sodium salt, potassium salt, calcium salt, barium salt, etc.], an ammonium salt, an organic salt [e.g. pyridine salt, triethylamine salt, etc.], or the like. Accordingly, suitable examples of the compound [IV] and its salt may be hydrogen azide, hydrazonic acid, sodium azide, potassium azide, lithium azide, calcium azide, barium azide, ammonium azide or the like.

This reaction is usually carried out in a conventional solvent which does not adversely influence the reaction such as water, methanol, ethanol, dioxane, N,N-dimethylformamide, methyl cellosolve, ethyl cellosolve or a mixture thereof.

The reaction temperature is not critical, and the reaction is usually carried out at ambient temperature or under warming or heating.

Process 7

The object compound [Ij] and its salt can be prepared by reacting a compound [Ii] or its salt with a compound [V], namely, alkylating agent.

Suitable examples of the alkylating agent [V] may be lower alkyl halide [e.g. methyl iodide, methyl bromide, methyl chloride, ethyl iodide, ethyl bromide, propyl iodide, butyl iodide, hexyl iodide, etc.], lower alkyl ester of sulfonic acid [e.g. methyl p-toluenesulfonate, ethyl p-toluenesulfonate, hexyl p-toluenesulfonate, methyl benzenesulfonate, methyl methanesulfonate, etc.], among which more suitable one is lower alkyl iodide, and the most suitable one is methyl iodide.

This reaction may be conducted in the presence or absence of a base such as alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal alkoxide [e.g. sodium methoxide, sodium ethoxide, potassium tert-butoxide, etc.] or the like.

This reaction is usually carried out in a conventional solvent which does not adversely influence the reaction such as methanol, ethanol, propanol, tetrahydrofuran, dioxan, methylene chloride, chloroform, dimethylformamide, dimethyl sulfoxide or the like.

The reaction temperature is not critical, and the reaction can be carried out under cooling to heating.

In this process, it is to be noted that the nitrogen atom at the first position of the pyrimidine ring in the compound [Ii] is alkylated and the group represented by $R^7$ is simultaneously removed in this reaction.

Process 8

The object compound [I] and its salt can be prepared by subjecting a compound [VI] or its salt to the introduction reaction of an amino or aryloxy group.

Suitable salts of the compound [VI] may be the same as those exemplified for the compound [I].

This reaction can be carried out by reacting the compound [VI] or its salt with an amino or phenol compound containing the group of $R^2$, namely a compound of the formula $R^2-H$.

The reaction may be conducted in the presence of a conventional organic or inorganic base.

The reaction is usually carried out in a conventional solvent which does not adversely influence the reaction such as methanol, ethanol, dioxane, methylenechloride. In case that the amino compound is liquid, it can also be used as a solvent.

The reaction temperature is not critical, and the reaction can be carried out under cooling to heating.

Process 9

The compound [I] and its salt can be prepared by subjecting a compound [VII] or its salt to the introduction reaction of an amino or aryloxy group.

Suitable salts of the compound [VII] may be the same as those exemplified for the compound [I].

The present introduction reaction can be conducted by converting the oxo group at the 4th position to a thioxo or halogeno group and then reacting the resultant compound with an amino or phenol compound containing the group of $R^2$.

The conversion of the oxo group to the thioxo group or halogeno group can be carried out by reacting the compound [VIII] or its salt with phosphorus pentasulfide or a halogenating agent as exemplified in Process 1.

The reaction of the resultant thioxo or halogeno compound with the amino or phenol compound can be conducted in substantially the same manner as that of Process 8.

Process 10

The object compound [Il] and its salt can be prepared by reacting a compound [Ik] or its salt with an alkylating agent.

The reaction of this process can be conducted in substantially the same manner as that of Process 7.

Accordingly, the alkylating agent and the reaction conditions are to be referred to those of Process 7.

Process 11

The compound [In] and its salt can be prepared by reducing a compound [Im] or its salt.

The reaction can be conducted substantially in the same manner as that of Process 2. Accordingly, the reaction mode and conditions can be referred thereto.

Process 12

The compound [Ip] and its salt can be prepared by acylating a compound [Io] or its salt.

The reaction can be conducted substantially in the same manner as that of Process 4. Accordingly, the reaction mode and conditions can be referred thereto.

When a compound [Io] or its salts is reacted with a lower alkylisocyanate, the compound [Ip] having lower alkylcarbamoyl group for the $R_b^5$ is obtained.

Process 13

The compound [Ir] and its salt can be prepared by acylating a compound [Iq] or its salt.

The reaction can be conducted substantially in the same manner to that of Process 4. Accordingly, the reaction mode and conditions can be referred thereto.

The object compounds [Ia] to [Ir] obtained by the above processes can be isolated and purified by a conventional manner such as extraction from the reaction mixture, recrystallization, column chromatography or the like.

When the object compounds [Ia] to [Ir] are obtained in a free form, they can be optionally converted into salts as mentioned before by a conventional manner.

Among the starting compounds in the above processes, the starting compound [II] are novel, and can be prepared by a method described in European Patent Application No. 84301741.9 (Publication No. 0123402). And further, the starting compounds [VI] and some of the starting compounds [VII] are also novel and can be prepared by the following processes or by similar manners to those of preparations and examples as exemplified below.

Process A

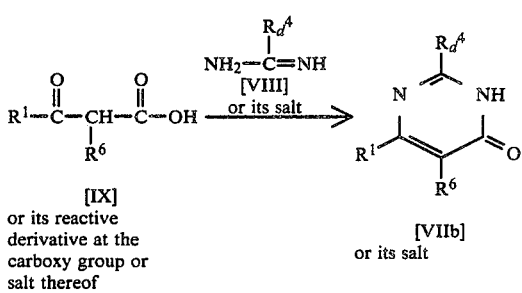

Process B

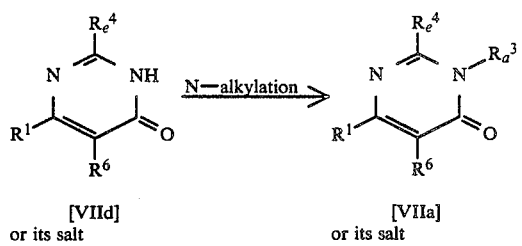

Process C

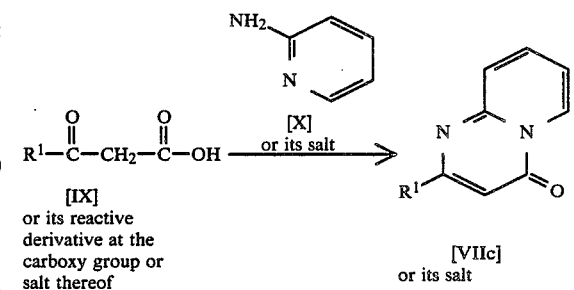

Process D

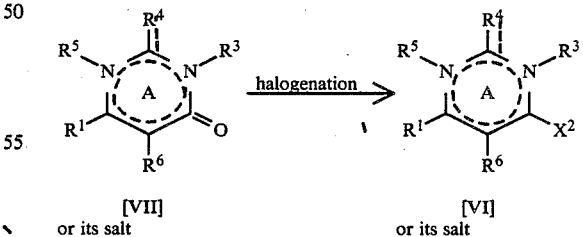

Process E

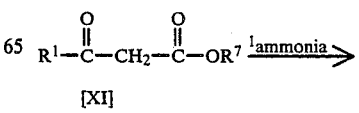

-continued

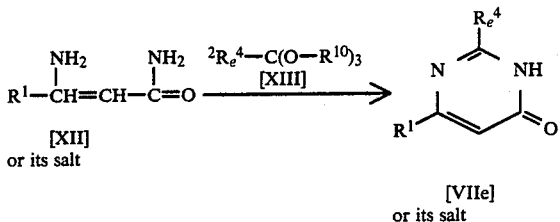

wherein
R$^1$, R$^3$, R$^4$, R$^5$, R$^6$, X$^2$ and the ⟵⟶ bond and the dotted line in the ring A are each as defined above;
R$_a^3$ is lower alkyl;
R$_d^4$ is lower alkyl;
R$_3^4$ is hydrogen or lower alkyl; and
R$^9$ and R$^{10}$ are each lower alkyl.

The processes for preparing the starting compounds and salts thereof are explained in detail in the following.

Process A

The compound [VIIb] and its salt can be prepared by reacting a compound [IX] or its reactive derivative at the carboxy group or a salt thereof with a compound [VIII] or its salt.

Suitable salts of the compounds [VIIb], [VIII] and [IX] may be the same as those exemplified for the compound [I].

Suitable reactive derivative at the carboxy group of the compound [IX] may include an ester, an acid halide, an acid anhydride and the like. These reactive derivatives can be optionally selected according to the kind of the compound [IX] to be used.

This reaction is usually carried out in a conventional solvent such as water, methanol, ethanol, propanol, tetralin, tetrahydrofuran, dioxan, chloroform, toluene, dimethylformamide, dimethylsulfoxide or any other organic solvent which does not adversely influence the reaction.

This reaction is preferably conducted in the presence of an acid such as inorganic acid [e.g. hydrochloric acid, sulfuric acid, polyphosphoric acid, etc.], organic acid [e.g. trifluoroacetic acid, benzenesulfonic acid, toluenesulfonic acid, etc.] or the like.

The reaction can also be conducted under dehydrating condition such as an azeotropic dehydration, in the presence of a dehydrating agent [e.g. magnesium sulfate, anhydrous zinc chloride, phosphorus pentoxide, zeolite, silica gel, etc.] or the like.

In case that the compound [IV] is used in a free acid form or its salt form, the reaction is preferably carried out in the presence of a conventional condensing agent.

The reaction temperature is not critical, and the reaction is usually carried out at ambient temperature or under warming or heating.

Process B

The compound [VIIa] and its salt can be prepared by reacting a compound [VIId] or its salt with an alkylating agent.

Suitable salts of the compound [VIIa] and [VIId] may be the same as those exemplified for the compound [I].

The reaction can be conducted in substantially the same manner as that of Process 7.

Accordingly, the alkylating agent and the reaction conditions are to be referred to those of Process 7.

Process C

The compound [VIIc] and its salt can be prepared by reacting a compound [IX] or its reactive derivative at the carboxy group or a salt thereof with a compound [X] or its salt.

Suitable salts of the compounds [VIIc], [IX] and [X] may be the same as those exemplified for the compound [I].

The reaction can be conducted in substantially the same manner as that of Process A. Accordingly, the reaction conditions are to be referred thereto.

Process D

The compound [VI] and its salt can be prepared by halogenating a compound [VII] or its salt.

Suitable salts of the compounds [VI] and [VII] may be the same as those exemplified for the compound [I].

The reaction can be conducted in substantially the same manner as that of Process 1. Accordingly, the reaction conditions are to be referred thereto.

Process E (1) The compound [XII] and its salt can be prepared by reacting a compound [XI] with ammonia.

Suitable salts of the compound [XII] may be the same as those exemplified for the compound [I].

The reaction is usually carried out in a solvent such as water, ethanol or any other solvent which does not adversely affect the reaction, preferably under cooing, at room temperature or under warming.

(2) The compound [VIIe] and its salt can be prepared by reacting a compound [XII] or its salt obtained in the above with a compound [XIII].

Suitable salts of the compound [VIIe] may be the same as those exemplified for the compound [I].

The reaction may be conducted in the presence of a conventional organic or inorganic acid.

The reaction is usually carried out in a solvent such as ethanol or any other solvent which does not adversely affect the reaction, preferably at room temperature, under warming or heating.

It is to be noted that some of the object compounds [I] and the starting compounds [II], [III] and [V] to [XIII] include one or more stereoisomers due to asymmetric carbon atom(s) and/or carbon-nitrogen double bond(s) in the molecule, and all of such isomers are included within the scope of this invention.

For the purpose of showing pharmaceutical activity of the pyrimidine derivatives [I], cardiotonic test data are illustrated in the following.

Test Method A

Cardiotonic activity

Mongrel dogs of either sex were anesthetized with sodium pentobarbital, 35 mg/kg, i.p. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure, from which dp/dt max was derived by analog computing. To measure the systemic blood pressure the left femoral artery was cannulated. The blood pressure pulse was used to trigger a heart rate meter. Another catheter was positioned in the vena cave through right femoral vein for injection of drugs.

Systemic blood pressure, left ventricular pressure, dp/dt max and heart rate were recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max changes (dp/dt M.C.) calculated by following formula, and are shown in table 1.

$$dp/dt\ M.C.(\%) = \left( \frac{dp/dt\ \text{max after dosing}}{dp/dt\ \text{max before dosing}} - 1 \right) \times 100$$

Test Results A

TABLE 1

| Test Compound (Example No.) | Dose (mg/kg) | dp/dt M.C. (%) |
|---|---|---|
| Example 1 | 0.1 | 45.0 |
| Example 2 | 0.1 | 114.0 |
| Example 3 | 0.1 | 29.0 |
| Example 11 | 0.1 | 60.0 |
| Example 12 | 0.1 | 152.0 |
| Example 18 | 0.1 | 72.0 |
| Examples (17-12) and (19-12) | 0.1 | 87.0 |
| Examples (17-6) and 20 | 0.1 | 76.0 |
| Amrinone* | 0.1 | 9.0 |

*3-Amino-5-(4-pyridyl)-2(1H)-pyridinone; known compound actually used as cardiotonic medicine.

Test Method B

Anti-platelet activity

Platelet rich plasma (PRP) which contains $6.5-7.5 \times 10^8$ platelet/ml was prepared from rabbit blood. To the 200 μl of PRP, 5 μl of calcium chloride (1 mM) and 50 μl of pH 7.4 Tris-acetate solution (5 mM) containing 120 mM NaCl and test compound were added successively, and then stirred for 2 min. at 37° C. To the solution 5 μl of adenosine diphosphate (ADP) (2.5 μM) or collagen (2.5 μg/ml) was added as an agregation inducer. Aggregation was measured by using an aggregometer (NKK HEMA TRACER 1). $ID_{50}$ is shown in Table 2.

Test Results B

TABLE 2

| Test Compound (Example No.) | $ID_{50}$ (Mol) ADP | $ID_{50}$ (Mol) Collagen |
|---|---|---|
| Example 2 | $2.6 \times 10^{-7}$ | $3.6 \times 10^{-7}$ |

Test Method C

Antihypertensive activity

Five-week old male Wistar rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150-200 mmHg were used for experiment between 5 and 7 weeks after surgery.

The test compounds were administered orally. Blood pressure was measured at the femoral artery by means of a pressure transducer and recorded as electrically integrated values of mean arterial pressure.

Test Results C

Mean ratios of maximum decrease of blood pressure (mmHg) are shown in table 3.

TABLE 3

| Test Compound (Example No.) | Dose (mg/kg) | Effect Max (%) |
|---|---|---|
| Example 2 | 1.0 | 39.0 |

As being apparent from the above test results, the object compound [I] of the present invention are useful as cardiotonics, antihypertensive agents, cerebrovascular vasodilator and anti-platelet agents.

For therapeutic administration, the object compounds [I] of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral of external administration. The pharmaceutical preparation may be compounded in a solid form such as capsule, tablet, dragee or suppository, or in a liquid form such as solution, suspension or emulsion. If needed, there may be included in the above preparation auxiliary substance, stabilizing agent, wetting or emulsifying agent, buffer or any other commonly used additives.

The pharmaceutical composition for cardiac, antihypertensive, cerebrovascular vasodilation, anti-platelet aggregation or antiallergic contains an effective amount of the compound [I] or its salts.

The effective ingredient may usually be administered with a unit dose of 0.01 mg/kg to 500 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

To the solution of acetamidine hydrochloride (28.11 g) in methanol (200 ml) was added sodium methoxide (17.7 g), and stirred at ambient temperature for 10 minutes. The resulting suspension was evaporated, and ethanol (200 ml) was added. To the resulting suspension was added ethyl veratroylacetate (50.0 g) in toluene (300 ml), and distilled until the temperature comes to 110° C. Then additional toluene (400 ml) was added and refluxed under azeotropic condition for 3 hours. After cooled, the resulting suspension was dissolved in chloroform, washed with water, and dried over sodium bicarbonate. After eveporated, the residue was crystallized from ethyl acetate-diisopropyl ether (1:1 v/v) to give 3,4-dihydro-6-(3,4-dimethoxyphenyl)-2-methylpyrimidin-4-one (33.6 g).

mp. 228°–235° C.

IR (Nujol): 1650 cm$^{-1}$.

NMR (CDCl$_3$-CD$_3$OD, δ): 7.8–7.5 (2H, m), 6.94 (1H, d, J=8 Hz), 6.69 (1H, s), 4.01 (3H, s), 3.96 (3H, s), 2.55 (3H, s).

Preparation 2

To a suspension of 3,4-dihydro-6-(3,4 dimethoxyphenyl)-2-methylpyrimidin-4-one (2.0 g) in N,N-dimethylformamide (20 ml) were added potassium tert-.butoxide (1.08 g) and methyl iodide (1.0 ml), and stirred at ambient temperature for an hour. Resulting mixture was poured into water, and extracted with ethyl acetate. The organic layer was chromatographed on silica gel eluting with chloroform to give 3,4-dihydro-6-(3,4-dimethoxyphenyl)-2,3-dimethylpyrimidin-4-one (1.38 g).

mp. 187°–190° C.

IR (Nujol): 1670 cm$^{-1}$.

NMR (CDCl$_3$, δ): 7.4–7.6 (2H, m), 6.88 (1H, d, J=9 Hz), 6.68 (1H, s), 3.95 (3H, s), 3.93 (3H, s), 3.55 (3H, s), 2.61 (3H, s).

Preparation 3

A suspension of 3,4-dihydro-6-(3,4-dimethoxyphenyl)-2-methylpyrimidin-4-one (2.4 g) in phosphorus oxychloride (20 ml) was refluxed for 2 hours, and evaporated. To the residue were added aqueous sodium bicarbonate solution and chloroform, and stirred at ambient temperature for 2 hours. The organic layer was obtained and washed with water. After evaporated, the residue was dissolved in ethyl acetate-diisopropyl ether mixture (1:6 v/v). The precipitates were filtered off, and the filtrate was evaporated to give 4-chloro-6-(3,4-dimethoxyphenyl)-2-methylpyrimidine (2.09 g).

mp. 84°–87° C.

IR (Nujol): 1570, 1515 cm$^{-1}$.

NMR (CDCl$_3$, δ): 7.4–7.8 (3H, m), 6.97 (1H, d, J=8 Hz), 3.97 (3H, s), 3.94 (3H, s), 2.75 (3H, s).

Preparation 4

Ethyl veratroylacetate (4.5 g) was added dropwise under stirring at 60°–70° C. to a suspension of 2-aminopyridine (0.84 g) in polyphosphoric acid (13.7 g). The reaction mixture was stirred at 100° C. for 3 hrs and poured into ice-water (50 ml). The aqueous solution was extracted with chloroform, washed with water, dried and evaporated to give dark oily residue which was chromatographed on silica gel using n-hexaneethyl acetate. The fractions were evaporated and the resulting residue was triturated with ethanol-isopropyl ether to give 2-(3,4-dimethoxyphenyl)-4-oxo-4H-pyrido[1,2-a]pyrimidine (3.8 g).

mp: 165°–167° C.

IR (Nujol): 1675, 1630 cm$^{-1}$.

NMR (DMSO-d$_6$, δ): 3.87 (3H, s), 3.90 (3H, s), 6.88–7.27 (3H, m), 7.43–7.92 (4H, m), 9.01 (1H, q, J=7 Hz, 1.5 Hz).

Preparation 5

(i) A suspension of ethyl veratroylacetate (100 g) in ammonia water (28%, 1000 ml) was stirred at ambient temperature for 6 days. The precipitates were filtered, washed with ethanol and disopropyl ether, and dried in the air, to give 2-amino-3',4'-dimethoxycinnamamide (40.98 g)

mp: 204°–207° C.

IR (Nujol): 1640, 1610, 1580 cm$^{-1}$.

NMR (DMSO-d$_6$, δ): 7.35 (2H, br s), 6.8–7.2 (3H, m), 6.28 (2H, br s), 4.80 (1H, s), 3.79 (6H, s).

(ii) To a suspension of 2-amino-3',4'-dimethoxycinnamamide (2.5 g) in ethanol (150 ml) were added ethyl orthoformate (38 ml) and conc. hydrochloric acid (4 ml), and refluxed for 2.5 hours.

To the suspension was added ethyl orthoformate (56 ml) again, and refluxed for 2 hours. The resulting solution was evaporated, and dissolved in chloroform. The solution was washed with aqueous sodium bicarbonate solution, dried over sodium sulfate, and evaporated under reduced pressure.

The resulting syrup was triturated with ethyl acetate to give 3,4-dihydro -6-(3,4-dimethoxyphenyl)-4-pyrimidone (1.05 g).

mp: 248°–249° C.

IR (Nujol): 1680, 1650 cm$^{-1}$.

NMR (CDCl$_3$-MeOH-d$_4$, δ): 8.17 (1H, s), 7.4–7.7 (2H, m), 6.96 (1H, d, J=9 Hz), 6.81 (1H, s), 3.96 (6H, s), 3.77 (1H, br s).

Preparation 6

The following compounds were prepared according to a similar manner to that of Preparation 3.

(1) 4-Chloro-6-(3,4-dimethoxyphenyl)pyrimidine

IR (Nujol): 1675, 1600 cm$^{-1}$.

NMR (CDCl$_3$, δ): 8.97 (1H, s), 7.3–7.8 (3H, m), 6.96 (1H, d, J=8 Hz), 3.96 (3H, s), 3.94 (3H, s).

(2) 4-Chloro-2-methyl-6-(4-pyridyl)pyrimidine mp: 99°–102° C.

IR (Nujol): 1570, 1530 cm$^{-1}$.

NMR (CDCl$_3$, δ): 8.74 (2H, d, J=7 Hz), 7.88 (2H, d, J=7 Hz), 7.57 (1H, s), 2.79 (3H, s)

(3)
4-Chloro-5-(3,4-dimethoxyphenyl)-2-methylpyrimidine mp: 72°–75° C.

IR (Nujol): 1570 cm$^{-1}$.

NMR (CDCl$_3$, δ): 8.56 (1H, s), 7.00 (3H, s), 3.96 (3H, s), 3.93 (3H, s), 2.76 (3H, s).

(4)
4-Chloro-6-(3,4-dimethoxyphenyl)-2,5-dimethylpyrimidine mp: 91°–94° C.

IR (Nujol): 1560, 1510 cm$^{-1}$.

NMR (CDCl$_3$, δ): 7.2–6.8 (3H, m), 3.95 (6H, s), 2.71 (3H, s), 2.40 (3H, s).

Preparation 7

The following compounds were prepared according to a similar manner to that of Preparation 1.

(1) 3,4-Dihydro-2-methyl-6-(4-pyridyl)pyrimidin-4-one mp: >300° C.

IR (Nujol): 1680, 1610 cm$^{-1}$.

NMR (D$_2$O-DCl, δ): 9.06 (2H, d, J=7 Hz), 8.54 (2H, d, J=7 Hz), 7.12 (1H, s), 2.66 (3H, s).

(2)
3,4-Dihydro-5-(3,4-dimethoxyphenyl)-2-methylpyrimidin-4-one mp: 198°–200° C.

IR (Nujol): 1660, 1600 cm$^{-1}$.

NMR (CDCl$_3$, δ): 13.40 (1H, br s), 8.07 (1H, s), 7.4–7.0 (2H, m), 6.87 (1H, d, J=8 Hz), 3.87 (6H, s), 2.48 (3H, s).

(3)
3,4-Dihydro-6-(3,4-dimethoxyphenyl)-2,5-dimethylpyrimidin-4-one mp: 205°–215° C.

IR (Nujol): 1670 cm$^{-1}$.

NMR (CDCl$_3$, δ): 13.7–12.9 (1H, br s), 7.3–6.8 (3H, m), 3.92 (6H, s), 2.53 (3H, s), 2.17 (3H, s).

Preparation 8

The following compounds were prepared according to a similar manner to that of Preparation 2.

(1)

3,4-Dihydro-6-(3,4-dimethoxyphenyl)-2-ethyl-3-methylpyrimidin-4-one mp: 180°–184° C.
IR (Nujol): 1670, 1600 cm$^{-1}$.
NMR (CDCl$_3$, δ): 7.58 (1H, dd, J=8 Hz, J=2 Hz), 7.53 (1H, d, J=2 Hz), 6.87 (1H, d, J=8 Hz), 6.66 (1H, s), 3.93 (6H, s), 3.52 (3H, s), 2.80 (2H, q, J=7 Hz), 1.40 (3H, t, J=7 Hz)

(2)

3,4-Dihydro-6-(3,4-dimethoxyphenyl)-3-ethyl-2-methylpyrimidin-4-one mp: 129°–132° C.
IR (Nujol): 1660, 1600 cm$^{-1}$.
NMR (CDCl$_3$, δ): 7.4–7.7 (2H, m), 6.90 (1H, d, J=9 Hz), 6.66 (1H, s), 4.10 (2H, q, J=7 Hz), 3.93 (3H, s), 3.90 (3H, s), 2.61 (3H, s), 1.34 (3H, t, J=7 Hz).

(3)

3,4-Dihydro-6-(3,4-dimethoxyphenyl)-3-methylpyrimidin-4-one mp: 175°–178° C.
IR (Nujol): 1680, 1600 cm$^{-1}$.
NMR (CDCl$_3$, δ): 8.10 (1H, s), 7.4–7.6 (2H, m), 6.89 (1H, d, J=9 Hz), 6.77 (1H, s), 3.93 (3H, s), 3.90 (3H, s), 3.54 (3H, s).

(4)

3,4-Dihydro-6-(3,4-dimethoxyphenyl)-2,3,5-trimethylpyrimidin-4-one mp: 115°–118° C.
IR (Nujol): 1650, 1600 cm$^{-1}$.
NMR (CDCl$_3$, δ): 7.3–6.8 (3H, m), 3.93 (6H, s), 3.57 (3H, s), 2.56 (3H, s), 2.16 (3H, s).

(5)

3,4-Dihydro-6-(3,4-dimethoxyphenyl)-3-ethylpyrimidin-4-one mp: 150°–153° C.
IR (Nujol): 1670, 1680 cm$^{-1}$.
NMR (CDCl$_3$, δ): 8.10 (1H, s), 7.7–7.4 (2H, m), 6.96 (1H, d, J=9 Hz), 6.76 (1H, s), 3.98 (2H, q, J=7 Hz), 3.96 (6H, s), 1.41 (3H, t, J=7 Hz).

Preparation 9

The following compound was prepared according to a similar manner to that of Preparation 5.

3,4-Dihydro-6-(3,4-dimethoxyphenyl)-2-ethylpyrimidin-4-one mp: 195°–200° C.
IR(Nujol): 1670, 1600 cm$^{-1}$.

EXAMPLE 1

To 3,4-dihydro-6-(3,4-dimethoxyphenyl)-3-methyl-4-(2,4,6-trimethylphenylimino)-2-(1H)pyrimidone (5.0 g) was added phosphorus oxychloride (50 ml). The mixture was refluxed for 7 hours and evaporated under reduced pressure. The resulting syrup was triturated in a mixture of ice and water, neutralized with aqueous sodium bicarbonate and extracted with chloroform. The extract was dried and evaporated under reduced pressure. The residue was chromatographed on silica gel using chloroform to give 2-chloro-3,4-dihydro-6-(3,4-dimethoxyphenyl)-3-methyl-4-(2,4,6-trimethylphenylimino)pyrimidine (3.26 g).

mp: 159°–162° C.
IR (Nujol), cm$^{-1}$: 1640, 1590.
NMR (CDCl$_3$, δ): 7.40 (1H, d, J=2 Hz), 7.27 (1H, dd, J=2 Hz, J=9 Hz), 6.91 (2H, s), 6.86 (1H, d, J=9 Hz), 6.04 (1H, s), 3.92 (3H, s), 3.87 (3H, s), 3.83 (3H, s), 2.28 (3H, s), 2.05 (6H, s).

EXAMPLE 2

To a suspension of 2-chloro-3,4-dihydro-6-(3,4-dimethoxyphenyl)-3-methyl-4-(2,4,6-trimethylphenylimino)pyrimidine (1.5 g) in ethanol (20 ml) was added 10%-palladium on carbon (0.8 g). The mixture was stirred under hydrogen (1 atm) for 40 minutes. After removal of the catalyst by filtration, the filtrate was evaporated in vacuo. The residue was neutralized with aqueous sodium bicarbonate and extracted with ethyl acetate. The extract was dried over magnesium sulfate and evaporated in vacuo. The residue was chromatographed on silica gel using chloroform. The fractions containing the desired compound were combined and evaporated in vacuo to give a residue, which was recrystallized from ethyl acetate to afford 3,4-dihydro-6-(3,4-dimethoxyphenyl)-3-methyl-4-(2,4,6-trimethylphenylimino)pyrimidine (0.36 g).

mp 180°–182° C.
IR (Nujol, cm$^{-1}$): 1640, 1600.
NMR (CDCl$_3$, δ): 7.81 (1H, s), 7.29 (1H, d, J=2 Hz), 7.08 (1H, dd, J=2 Hz, J=8 Hz), 6.74 (2H, s), 6.68 (1H, d, J=8 Hz); 5.97 (1H, s), 3.84 (3H, s), 3.80 (3H, s), 3.53 (3H, s), 2.24 (3H, s), 2.00 (6H, s).

EXAMPLE 3

To a suspension of 2-chloro-3,4-dihydro-6-(3,4-dimethoxyphenyl)-3-methyl-4-(2,4,6-trimethylphenylimino)pyrimidine (1.5 g) in ethanol (15 ml) was added N-methylbenzylamine (1.47 ml). The mixture was refluxed for 5 hours. The resulting suspension was dissolved in chloroform, washed with brine, dried over magnesium sulfate and evaporated in vacuo. The obtained syrup was triturated in diisopropyl ether and filtered to afford 3,4-dihydro-6-(3,4-dimethoxyphenyl)-3-methyl-2-(N-methyl-N-benzylamino)-4-(2,4,6-trimethylphenylimino)pyrimidine (1.18 g).

mp 96°–98° C.
IR (Nujol, cm$^{-1}$): 1620, 1600.
NMR (CDCl$_3$, δ): 6.5–7.5 (10H, m), 5.86 (1H, s), 4.58 (2H, s), 3.85 (3H, s), 3.82 (3H, s), 3.78 (3H, s), 2.93 (3H, s), 2.28 (3H, s), 2.08 (6H, s).

EXAMPLE 4

3,4-Dihydro-6-(3,4-dimethoxyphenyl)-2-dimethylamino-3-methyl-4-(2,4,6-trimethylphenylimino)pyrimidine (1.82 g) was obtained according to a similar manner to that of Example 3 from 2-chloro-3,4-dihydro-6-(3,4-dimethoxyphenyl)-3-methyl-4-(2,4,6-trimethylphenylimino)pyrimidine (30 g) and 50% aqueous solution of dimethylamine (3.4 ml).

mp 124°–125° C.
IR (Nujol, cm$^{-1}$): 1640.
NMR (CDCl$_3$, δ): 7.53 (1H, d, J=2 Hz), 7.30 (1H, dd, J=2 Hz, J=5.5 Hz), 6.86 (2H, s), 6.82 (1H, d, J=5.5 Hz), 5.81 (1H, s), 3.85 (3H, s), 3.83 (3H, s), 3.62 (3H, s), 2.94 (6H, s), 2.24 (3H, s), 2.01 (6H, s).

EXAMPLE 5

3,4-Dihydro-6-(3,4-dimethoxyphenyl)-3-methyl-2-(N-methylanilino)-4-(2,4,6-trimethylphenylimino)-pyrimidine (2.47 g) was obtained according to a similar manner to that of Example 3 from 2-chloro-3,4-dihydro-6-(3,4-dimethoxyphenyl)-3-methyl-4-(2,4,6-trimethylphenylimino)pyrimidine (3.0 g) and N-methylaniline (2.45 ml).

mp 164°–165° C.
IR (Nujol, cm$^{-1}$): 1635.
NMR (CDCl$_3$, δ): 7.6–6.6 (10H, m), 5.90 (1H, s), 3.86 (6H, s), 3.48 (3H, s), 3.20 (3H, s), 2.26 (3H, s), 2.03 (6H, s).

EXAMPLE 6

To a suspension of 2-chloro-3,4-dihydro-6-(3,4-dimethoxyphenyl)-3-methyl-4-(2,4,6-trimethylphenylimino)-pyrimidine (1.07 g) in ethanol (10 ml) was added piperazine (0.70 g). The mixture was refluxed for 3 hours, cooled to ambient temperature. The mixture was evaporated, and the residue was dissolved in chloroform and washed with aqueous sodium bicarbonate solution. The organic layer was dried over magnesium sulfate and evaporated. The residue was chromatographed on silica gel using a mixture of chloroform and methanol (95:5) to give 3,4-dihydro-6-(3,4-dimethoxyphenyl)-3-methyl-2-(1-piperazinyl)-4-(2,4,6-trimethylphenylimino)pyrimidine (0.69 g).

mp 185°–189° C.
IR (Nujol, cm$^{-1}$) 1630, 1540, 1520.
NMR (CDCl$_3$, δ): 7.0–7.2 (2H, m), 6.5–6.8 (3H, m), 5.76 (1H, s), 3.79 (6H, s), 3.66 (3H, s), 3.3 (4H, br. s), 3.0 (4H, br. s), 2.23 (3H, s), 2.02 (6H, s).

EXAMPLE 7

To a suspension of 2-chloro-3,4-dihydro-6-(3,4-dimethoxyphenyl)-3-methyl-4-(2,4,6-trimethylphenylimino)-pyrimidine (10.0 g) in chloroform (100 ml) was added hydrazine hydrate (3.66 ml). The mixture was refluxed for 6 hours. The reaction mixture was evaporated in vacuo. The residue was chromatographed on silica gel using chloroform to give 3,4-dihydro-6-(3,4-dimethoxyphenyl)-2-hydrazino-3-methyl-4-(2,4,6-trimethylphenylimino)pyrimidine (3.46 g).

mp >300° C.
IR (Nujol, cm$^{-1}$): 1645, 1635, 1590.
NMR (CDCl$_3$-CD$_3$OD, δ): 6.8–7.2 (5H, m), 5.22 (1H, s), 3.87 (6H, s), 3.57 (3H, s), 3.2–4.2 (3H, br. m), 2.27 (3H, s), 2.05 (6H, s).

EXAMPLE 8

To a suspension of 2-chloro-3,4-dihydro-6-(3,4-dimethoxyphenyl)-3-methyl-4-(2,4,6-trimethylphenylimino)-pyrimidine (3.0 g) in chloroform (15 ml) was added formylhydrazine (1.36 g). The mixture was refluxed for 6 hours and cooled to ambient temperature. The resulting precipitates were filtered off and the filtrate was evaporated in vacuo. The residue was chromatographed on silica gel using chloroform to give 3,4-dihydro-6-(3,4-dimethoxyphenyl)-2-(2-formylhydrazino)-3-methyl-4-(2,4,6-trimethylphenylimino)pyrimidine (0.84 g).

mp 136°–143° C.
IR (Nujol, cm$^{-1}$): 1680, 1590.
NMR (CDCl$_3$, δ): 7.94 (1H, s), 6.8–7.5 (5H, m), 5.10 (1H, s), 3.85 (6H, s), 3.8 (3H, s), 2.27 (3H, s), 2.17 (6H, s).

EXAMPLE 9

To a suspension of 2-chloro-3,4-dihydro-6-(3,4-dimethoxyphenyl)-3-methyl-4-(2,4,6-trimethylphenylimino)-pyrimidine (5.0 g) in dry ethanol (50 ml) was added sodium methylmercaptate (1.06 g). The mixture was stirred at ambient temperature for 3 hours, poured into water (100 ml) and extracted with chloroform. The extract waas dried over magnesium sulfate, and chromatographed on silica gel using chloroform as an eluent. After evaporation under reduced pressure, the residue was triturated with ethyl acetate to give 3,4-dihydro-6-(3,4-dimethoxyphenyl)-3-methyl-2-methylthio-4-(2,4,6-trimethylphenylimino)pyrimidine (3.51 g).

mp 172°–173° C.
IR (Nujol, cm$^{-1}$) 1640.
NMR (CDCl$_3$, δ): 7.50 (1H, d, J=2 Hz), 7.32 (1H, dd, J=2 Hz, J=9 Hz), 6.88 (2H, s), 6.82 (1H, d, J=9 Hz), 5.92 (1H, s), 3.86 (6H, s), 3.69 (3H, s), 2.68 (3H, s), 2.28 (3H, s), 2.02 (6H, s).

EXAMPLE 10

To a suspension of 3,4-dihydro-6-(3,4-dimethoxyphenyl)-3-methyl-2-(1-piperazinyl)-4-(2,4,6-trimethylphenylimino)pyrimidine (0.31 g) in tetrahydrofuran (10 ml) were added triethylamine (0.11 ml) and 4-fluorobenzoyl chloride (0.69 ml). The mixture was stirred at ambient temperature for an hour and the reaction was quenched by adding methanol (5 ml). After evaporation of the solvent, the residue was dissolved in ethyl acetate. The solution was washed with water, dried over magnesium sulfate and evaporated in vacuo. The residue was chromatographed on silica gel using a mixture of chloroform and methanol (95:5) to give 3,4-dihydro-6-(3,4-dimethoxyphenyl)-2-[4-(4-fluorobenzoyl)piperazin-1-yl]-3-methyl-4-(2,4,6-trimethylphenylimino)-pyrimidine (0.34 g).

mp 117°–121° C.
IR (Nujol, cm$^{-1}$): 1630, 1540, 1520.
NMR (CDCl$_3$, δ): 6.6–7.6 (9H, m), 5.88 (1H, s), 3.84 (6H, s), 3.75 (4H, br. s), 3.67 (3H, s), 3.2–3.5 (4H, m), 2.27 (3H, s), 2.03 (6H, s).

EXAMPLE 11

The mixture of 3,4-dihydro-6-(3,4-dimethoxyphenyl)-2-(2-formylhydrazino)-3-methyl-4-(2,4,6-trimethylphenylimino)pyrimidine (0.81 g) and polyphosphoric acid (8.2 g, 116% as phosphoric acid) was stirred at 110° C. for 2 hours and cooled to ambient temperature. The reaction mixture was poured into water and neutralized with aqueous sodium hydroxide solution. The precipitates were collected by filtration and washed with water to give 7,8-dihydro-5-(3,4-dimethoxyphenyl)-8-methyl-7-(2,4,6-trimethylphenylimino)-1,2,4-triazolo[4,3-a]pyrimidine (0.65 g).

mp 125°–130° C.
IR (Nujol, cm$^{-1}$): 1655, 1570.
NMR (DMSO-d$_6$, δ): 8.58 (1H, s), 6.8–7.3 (5H, m), 5.40 (1H, s), 3.80 (6H, s), 3.73 (3H, s), 2.21 (3H, s), 1.99 (6H, s).

EXAMPLE 12

To a suspension of 2-chloro-3,4-dihydro-6-(3,4-dimethoxyphenyl)-3-methyl-4-(2,4,6-trimethylphenylimino)-pyrimidine (1.0 g) in a mixture of methanol (9 ml) and water (1.5 ml) was added sodium azide (0.163 g). The mixture was stirred at 50° to 55° C. for an hour. After removal of the solvent, the residue was washed with water and collected by filtration to give 4,5-dihydro-7-(3,4-dimethoxyphenyl)-4-methyl-5-(2,4,6-trimethylphenylimino)tetrazolo[1,5-a]pyrimidine (0.80 g).

mp 198°–200° C.

IR (Nujol, cm$^{-1}$): 1660.

NMR (CDCl$_3$, δ): 6.8–7.5 (5H, m), 5.90 (1H, s), 3.93 (9H, s), 2.33 (3H, s), 2.07 (6H, s).

EXAMPLE 13

To a solution of 3,4-dihydro-6-(3,4-dimethoxyphenyl)-3-methyl-2-(N-methyl-N-benzylamino)-4-(2,4,6-trimethylphenylimino)pyrimidine (1.0 g) in tetrahydrofuran (20 ml) was added methyl iodide (2.58 ml). The solution was refluxed for 10 hours and cooled to ambient temperature. The reaction mixture was evaporated in vacuo and the residue was chromatographed on silica gel using chloroform to give 2-benzylimino-6-(3,4-dimethoxyphenyl)-1,3-dimethyl-1,2,3,4-tetrahydro-4-(2,4,6-trimethylphenylimino)pyrimidine (0.62 g).

mp 97°–100° C.

IR (Nujol, cm$^{-1}$): 1570, 1550.

NMR (CDCl$_3$, δ): 6.7–7.7 (10H, m), 5.57 (1H, s), 5.03 (2H, s), 3.85 (3H, s), 3.84 (3H, s), 3.30 (3H, s), 3.25 (3H, s), 2.33 (3H, s), 2.12 (6H, s).

EXAMPLE 14

6-(3,4-Dimethoxyphenyl)-1,3-dimethyl-2-methylimino-4-(2,4,6-trimethylphenyl)-1,2,3,4-tetrahydropyrimidine (0.47 g) was obtained according to a similar manner to that of Example 13 from 3,4-dihydro-6-(3,4-dimethoxyphenyl)-2-dimethylamino-3-methyl-4-(2,4,6-trimethylphenylimino)pyrimidine (0.8 g) and methyl iodide (2.45 ml).

mp 150°–151° C.

IR (Nujol, cm$^{-1}$): 1570, 1550.

NMR (CDCl$_3$, δ): 7.63 (1H, d, J=2 Hz), 7.26 (1H, d, J=2 Hz, J=9 Hz), 6.97 (2H, s), 6.79 (1H, d, J=9 Hz), 5.54 (1H, s), 3.91 (3H, s), 3.86 (3H, s), 3.33 (3H, s), 3.27 (6H, s), 2.32 (3H, s), 2.10 (6H, s).

EXAMPLE 15

6-(3,4-Dimethoxyphenyl)-1,3-dimethyl-2-phenylimino-4-(2,4,6-trimethylphenylimino)-1,2,3,4-tetrahydropyrimidine (0.4 g) was obtained according to a similar manner to that of Example 13 from 3,4-dihydro-6-(3,4-dimethoxyphenyl)-2-(N-methylanilino)-3-methyl-4-(2,4,6-trimethylphenylimino)pyrimidine (0.4 g) and methyl iodide (2.66 ml).

mp 145°–147° C.

IR (Nujol, cm$^{-1}$) 1580, 1540, 1520.

NMR (CDCl$_3$, δ): 7.6–6.6 (10H, m), 5.65 (1H, s), 3.83 (3H, s), 3.80 (3H, s), 3.68 (3H, s), 3.26 (3H, s), 2.33 (3H, s), 2.10 (6H, s).

EXAMPLE 16

The mixture of 4-chloro-6-(3,4-dimethoxyphenyl)-2-methylpyrimidine (2.0 g) and 2,4,6-trimethylaniline (5.3 ml) was stirred at 120° C. for an hour. After cooled, the mixture was triturated with ethyl acetate. The precipitates were collected, and dissolved in chloroform. The solution was washed with aqueous sodium bicarbonate solution, dried over magnesium sulfate, and evaporated to give 6-(3,4-dimethoxyphenyl)-2-methyl-4-(2,4,6-trimethylphenylamino)pyrimidine (2.39 g).

mp. 168°–170° C.

IR (Nujol): 1600, 1580, 1520 cm$^{-1}$.

NMR (CDCl$_3$, δ): 7.55 (1H, d, J=2 Hz), 7.28 (1H, dd, J=2 Hz, J=8 Hz), 6.96 (2H, s), 6.80 (1H, d, J=8 Hz), 6.7–7.4 (1H, brs), 6.02 (1H, s), 3.92 (3H, s), 3.86 (3H, s), 2.51 (3H, s), 2.32 (3H, s), 2.19 (6H, s).

EXAMPLE 17

The following compounds were prepared according to the similar manner to that of Example 16.

(1)

6-(3,4-Dimethoxyphenyl)-4-(1-indolinyl)-2-methylpyrimidine mp. 123°–125° C.

IR (Nujol): 1580 cm$^{-1}$.

NMR (CDCl$_3$, δ): 8.42 (1H, d, J=8 Hz), 6.8–7.7 (6H, m), 6.70 (1H, s), 3.97 (3H, s), 3.90 (3H, s), 3.8–4.2 (2H, m), 3.0–3.4 (2H, m), 2.69 (3H, s).

(2)

2-Amino-3,4-dihydro-6-(3,4-dimethoxyphenyl)-3-methyl-4-(2,4,6-trimethylphenylimino)pyrimidine mp. 192°–195° C.

IR (Nujol): 1630, 1600 cm$^{-1}$.

(3)

3,4-Dihydro-6-(3,4-dimethoxyphenyl)-3-methyl-2-(1,2,3,6-tetrahydropyridin-1-yl)-4-(2,4,6-trimethylphenylimino)pyrimidine mp 161°–163° C.

IR (Nujol): 1640 cm$^{-1}$.

(4)

3,4-Dihydro-6-(3,4-dimethoxyphenyl)-2,3-dimethyl-4-(2,4,6-trimethylphenylimino)pyrimidine mp 163°–168° C.

IR (Nujol): 1630 cm$^{-1}$.

(5)

2-(3,4-Dimethoxyphenyl)-4-(2,4,6-trimethylphenylimino)-4H-pyrido[1,2-a]pyrimidine mp. 187°–191° C.

IR (Nujol): 1640, 1605 cm$^{-1}$ (6)

6-(3,4-Dimethoxyphenyl)-2-methyl-4-[N-methyl-N-(2,4,6-trimethylphenyl)amino]pyrimidine mp. 124°–125° C.

IR (Nujol): 1580 cm$^{-1}$.

(7)

6-(3,4-Dimethoxyphenyl)-4-(2,4,6-trimethylphenylamino]pyrimidine mp. 164°–166° C.

IR (Nujol): 1620, 1600, 1590 cm$^{-1}$.

NMR (CDCl$_3$, δ): 8.63 (1H, s), 7.61 (1H, d, J=2 Hz), 7.30 (1H, bd, J=2 H, 8 Hz), 6.97 (2H, s), 6.85 (1H, br s), 6.83 (1H, d, J=8 Hz), 6.27 (1H, s), 3.94 (3H, s), 3.89 (3H, s), 2.33 (3H, s), 2.21 (6H, s).

(8)

6-(3,4-Dimethoxyphenyl)-4-[N-methyl-N-(2,4,6-trimethylphenyl)amino]pyrimidine mp: 124°–126° C.

IR (Nujol): 1585, 1520 cm$^{-1}$.

(9)

3,4-Dihydro-6-(3,4-dimethoxyphenyl)-3-methyl-4-(2,4,6-trimethylphenylimino)pyrimidine hydrochloride mp: 165°–173° C.

IR (Nujol): 1630, 1580 cm$^{-1}$.

(10)

3,4-Dihydro-6-(3,4-dimethoxyphenyl)-3-methyl-4-(2,4,6-trimethylphenylimino)pyrimidine mp: 180°–182° C.
IR (Nujol): 1640, 1600 cm$^{-1}$.

(11)

1-Acetyl-6-(3,4-dimethoxyphenyl)-3-methyl-1,2,3,4-tetrahydro-4-(2,4,6-trimethylphenylimino)pyrimidine mp: 173°–175° C.
IR (Nujol): 1685, 1630 cm$^{-1}$.

(12)

3,4-Dihydro-6-(3,4-dimethoxyphenyl)-3-ethyl-2-methyl-4-(2,4,6-trimethylphenylimino)pyrimidine mp: 118°–120° C.
IR (Nujol): 1630 cm$^{-1}$.

(13)

4-[1-(1,2,3,6-Tetrahydro)pyridyl]-6-(3,4-dimethoxyphenyl)-2-methylpyrimidine mp: 112°–114° C.
IR (Nujol): 1610, 1585 cm$^{-1}$.
NMR (CDCl$_3$, δ): 7.3–7.6 (2H, m), 6.85 (1H, d, J=8 Hz), 6.55 (1H, s), 5.7–6.0 (2H, m), 3.7–4.2 (4H, m), 3.95 (3H, s), 3.89 (3H, s), 2.57 (3H, s), 2.0–2.5 (2H, m)

(14)

6-(3,4-Dimethoxyphenyl)-2-methyl-4-(1-piperazinyl)pyrimidine mp: 138°–140° C.
IR (Nujol): 1600, 1580 cm$^{-1}$.
NMR (CDCl$_3$, δ): 7.56 (1H, d, J=2 Hz), 7.46 (1H, dd, J=2 Hz, 8 Hz), 6.87 (1H, d, J=8 Hz), 6.59 (1H, s), 3.96 (3H, s), 3.90 (3H, s), 3.75–3.50 (2H, m), 3.05–2.80 (2H, m), 2.56 (3H, s).

(15)

4-[4-(2,4-Dichloro-5-sulfamoylbenzoyl)piperazin-1-yl]-6-(3,4-dimethoxyphenyl)-2-methylpyrimidine mp: 150°–160° C.
IR (Nujol): 1640, 1580 cm$^{-1}$.

(16)

6-(3,4-Dimethoxyphenyl)-3-methyl-1,2,3,4-tetrahydro-4-(2,4,6-trimethylphenylimino)pyrimidine mp: 165°–166° C.
IR (Nujol): 1620, 1605, 1590 cm$^{-1}$.

(17)

2-Methyl-6-(4-pyridyl)-4-(2,4,6-trimethylphenylamino)pyrimidine mp: 154°–156° C.
IR (Nujol): 1590 cm$^{-1}$.
NMR (CDCl$_3$, δ): 8.60 (2H, br s), 7.65 (2H, br. d, J=5 Hz), 6.95 (2H, s), 6.31 (1H, s), 2.52 (3H, s), 2.33 (3H, s), 2.20 (6H, s).

(18)

3,4-dihydro-6-(3,4-dimethoxyphenyl)-2-ethyl-3-methyl-4-(2,4,6-trimethylphenylimino)pyrimidine mp: 198°–199° C.
IR (Nujol): 1630 cm$^{-1}$.

(19)

4,5-Dihydro-7-(3,4-dimethoxyphenyl)-4-methyl-5-(2,4,6-trimethylphenylimino)tetrazolo[1,5-a]pyrimidine hydrochloride mp: 221° C. (dec.).
IR (Nujol): 1635, 1595, 2380 cm$^{-1}$.

(20)

5-(3,4-Dimethoxyphenyl)-2-methyl-4-(2,4,6-trimethylphenylamino)pyrimidine mp: 202°–204° C.
IR (Nujol): 1590, 1550.
NMR (CDCl$_3$, δ): 8.10 (1H, s), 7.10–6.85 (5H, m), 6.20 (1H, br s), 3.92 (6H, s), 2.44 (3H, s), 2.29 (3H, s), 2.14 (6H, s).

(21)

6-(3,4-Dimethoxyphenyl)-2,5-dimethyl-4-(2,4,6-trimethylphenylamino)pyrimidine mp: 168°–170° C.
IR (Nujol): 1580, 1520 cm$^{-1}$.
NMR (CDCl$_3$, δ): 7.30–6.80 (5H, m), 5.89 (1H, br s), 3.93 (6H, s), 2.45 (3H, s), 2.33 (3H, s), 2.26 (9H, s).

(22)

6-(3,4-Dimethoxyphenyl)-4-(4-benzhydrylpiperazin-1-yl)-2-methylpyrimidine mp: 179°–181° C.
IR (Nujol): 1580, 1520 cm$^{-1}$.
NMR (CDCl$_3$, δ): 7.6–7.0 (12H, m), 6.83 (1H, d, J=9 Hz), 6.54 (1H, s), 4.24 (1H, s), 3.94 (3H, s), 3.88 (3H, s), 3.8–3.5 (4H, m), 2.56 (3H, s), 2.6–2.3 (4H, m).

EXAMPLE 18

A suspension of 3,4-dihydro-6-(3,4-dimethoxyphenyl)-2,3-dimethylpyrimidin-4-one (0.33 g) in phosphorus oxychloride (10 ml) was refluxed for an hour, and evaporated. To the residue was added 2,4,6-trimethylaniline (3.6 ml), and stirred at 100° C. for 2 hours. After cooled, the mixture was dissolved in chloroform, and washed with aqueous sodium bicarbonate solution.

The organic layer was dried over sodium sulfate, and chromatographed on silica gel, sluting with chloroform to give 3,4-dihydro-6-(3,4-dimethoxyphenyl)-2,3-dimethyl-4-(2,4,6-trimethylphenylimino)pyrimidine (0.21 g).

mp: 163°–168° C.
IR (Nujol): 1630 cm$^{-1}$.
NMR (CDCl$_3$, δ): 7.42 (1H, d, J=2 Hz), 7.20 (1H, dd, J=2 Hz, J=7 Hz), 6.85 (2H, s), 6.77 (1H, d, J=7 Hz), 5.98 (1H, s), 3.89 (3H, s), 3.85 (3H, s), 3.66 (3H, s), 2.57 (3H, s), 2.26 (3H, s), 2.03 (6H, s).

EXAMPLE 19

The following compounds were prepared according to the similar manners to that of Example 18.

(1)

2-(3,4-Dimethoxyphenyl)-4-(2,4,6-trimethylphenylimino)-4H-pyrido[1,2-a]pyrimidine mp: 187°–191° C.
IR (Nujol): 1640, 1605 cm$^{-1}$.
NMR (CDCl$_3$, δ): 9.46 (1H, d, J=7 Hz), 6.7–7.6 (8H, m), 6.07 (1H, s), 3.93 (3H, s), 3.87 (3H, s), 2.28 (3H, s), 2.07 (6H, s).

(2)
2-Amino-3,4-dihydro-6-(3,4-dimethoxyphenyl)-3-methyl-4-(2,4,6-trimethylphenylimino)pyrimidine mp: 192°–195° C.
IR (Nujol): 1630, 1600 cm$^{-1}$.

(3)
3,4-Dihydro-6-(3,4-dimethoxyphenyl)-3-methyl-2-(1,2,3,6-tetrahydropyridin-1-yl)-4-(2,4,6-trimethylphenylimino)pyrimidine mp: 161°–163° C.
IR (Nujol): 1640 cm$^{-1}$.

(4)
6-(3,4-Dimethoxyphenyl)-2-methyl-4-[N-methyl-N-(2,4,6-trimethylphenyl)amino]pyrimidine mp: 124°–125° C.
IR (Nujol): 1580 cm$^{-1}$.
NMR (CDCl$_3$, δ): 7.51 (1H, d, J=2 Hz), 7.15 (1H, dd, J=2 Hz, 8 Hz), 6.95 (2H, s), 6.78 (1H, d, J=8 Hz), 5.93 (1H, s), 3.91 (3H, s), 3.84 (3H, s), 3.36 (3H, s), 2.65 (3H, s), 2.32 (3H, s), 2.07 (6H, s).

(5)
6-(3,4-Dimethoxyphenyl)-2-methyl-4-(2,4,6-trimethylphenylamino)pyrimidine mp: 168°–170° C.
IR (Nujol): 1600, 1580, 1520 cm$^{-1}$.

(6)
6-(3,4-Dimethoxyphenyl)-4-(1-indolinyl)-2-methylpyrimidine mp: 123°–125° C.
IR (Nujol): 1580 cm$^{-1}$.

(7)
6-(3,4-Dimethoxyphenyl)-4-(2,4,6-trimethylphenylamino)pyrimidine mp: 164°–166° C.
IR (Nujol): 1620, 1600, 1590 cm$^{-1}$.

(8)
6-(3,4-Dimethoxyphenyl)-4-[N-methyl-N-(2,4,6-trimethylphenyl)amino]pyrimidine mp: 124°–126° C.
IR (Nujol): 1585, 1520 cm$^{-1}$.

(9)
3,4-Dihydro-6-(3,4-dimethoxyphenyl)-3-methyl-4-(2,4,6-trimethylphenylimino)pyrimidine hydrochloride mp: 165°–173° C.
IR (Nujol): 1630, 1580 cm$^{-1}$.

(10)
3,4-Dihydro-6-(3,4-dimethoxyphenyl)-3-methyl-4-(2,4,6-trimethylphenylimino)pyrimidine mp: 180°–182° C.
IR (Nujol): 1640, 1600 cm$^{-1}$.

(11)
1-Acetyl-6-(3,4-dimethoxyphenyl)-3-methyl-1,2,3,4-tetrahydro-4-(2,4,6-trimethylphenylimino)pyrimidine mp: 173°–175° C.
IR (Nujol): 1685, 1630 cm$^{-1}$.

(12)
3,4-Dihydro-6-(3,4-dimethoxyphenyl)-3-ethyl-2-methyl-4-(2,4,6-trimethylphenylimino)pyrimidine mp: 118°–120° C.
IR (Nujol): 1630 cm$^{-1}$.
NMR (CDCl$_3$, δ): 7.5–6.6 (5H, m), 5.96 (1H, s), 4.32 (2H, q, J=7 Hz), 3.86 (3H, s), 3.83 (3H, s), 2.60 (3H, s), 2.25 (3H, s), 2.04 (6H, s), 1.46 (3H, t, J=7 Hz).

(13)
4-[1-(1,2,3,6-Tetrahydro)pyridyl]-6-(3,4-dimethoxyphenyl)-2-methylpyrimidine mp: 112°–114° C.
IR (Nujol): 1610, 1585 cm$^{-1}$.

(14)
6-(3,4-Dimethoxyphenyl)-2-methyl-4-(1-piperazinyl)pyrimidine mp: 138°–140° C.
IR (Nujol): 1600, 1580 cm$^{-1}$.

(15)
4-[4-(2,4-Dichloro-5-sulfamoylbenzoyl)piperazin-1-yl]-6-(3,4-dimethoxyphenyl)-2-methylpyrimidine mp: 150°–160° C.
IR (Nujol): 1640, 1580 cm$^{-1}$.

(16)
6-(3,4-Dimethoxyphenyl)-3-methyl-1,2,3,4-tetrahydro-4-(2,4,6-trimethylphenylimino)pyrimidine mp: 165°–166° C.
IR (Nujol): 1620, 1605, 1590 cm$^{-1}$.

(17)
2-Methyl-6-(4-pyridyl)-4-(2,4,6-trimethylphenylamino)pyrimidine mp: 154°–156° C.
IR (Nujol): 1590 cm$^{-1}$.

(18)
3,4-Dihydro-6-(3,4-dimethoxyphenyl)-2-ethyl-3-methyl-4-(2,4,6-trimethylphenylimino)pyrimidine mp: 198°–199° C.
IR (Nujol): 1630 cm$^{-1}$.
NMR (CDCl$_3$, δ): 7.50 (1H, d, J=2 Hz), 7.25 (1H, dd, J=9 Hz), 6.84 (2H, s), 6.79 (1H, d, J=9 Hz), 6.00 (1H, s), 3.89 (3H, s), 3.86 (3H, s), 3.65 (3H, s), 2.82 (2H, q, J=8 Hz), 2.27 (3H, s), 2.03 (6H, s), 1.42 (3H, t, J=8 Hz).

(19)
4,5-Dihydro-7-(3,4-dimethoxyphenyl)-4-methyl-5-(2,4,6-trimethylphenylimino)tetrazolo[1,5-a]-pyrimidine hydrochloride mp: 221° C. (dec.).
IR (Nujol): 1635, 1595, 2380 cm$^{-1}$.

(20)
5-(3,4-Dimethoxyphenyl)-2-methyl-4-(2,4,6-trimethylphenylamino)pyrimidine mp: 202°–204° C.
IR (Nujol): 1590, 1550 cm$^{-1}$.

(21)
6-(3,4-Dimethoxyphenyl)-2-methyl-4-(2,4,6-trimethylphenoxy)pyrimidine mp: 122°–125° C.
IR (Nujol): 1580 cm$^{-1}$.

(22)
3,4-Dihydro-6-(3,4-dimethoxyphenyl)-3-ethyl-4-(2,4,6-trimethylphenylimino)pyrimidine mp: 111°–113° C.
IR (Nujol): 1640 cm$^{-1}$.
NMR (CDCl$_3$, δ): 7.96 (1H, s), 7.77 (1H, d, J=2 Hz), 7.22 (1H, dd, J=8 Hz, J=2 Hz), 6.89 (2H, s), 6.80 (1H, d, J=8 Hz), 6.09 (1H, s), 4.13 (2H, q, J=7 Hz), 3.93 (3H, s), 3.90 (3H, s), 2.30 (3H, s), 2.08 (6H, s), 1.50 (3H, t, J=7 Hz).

EXAMPLE 20

To a solution of 6-(3,4-dimethoxyphenyl)-2-methyl-4-(2,4,6-trimethylphenylamino)pyrimidine (1.0 g) in N,N-dimethylformamide (15 ml) were added potassium tert-butoxide (0.37 g) and methyl iodide (0.34 ml), and the mixture was stirred at ambient temperature for 1.5 hours. Then the mixture was poured into ice-water (200 ml) and stirred for an hour. The precipitates were collected, washed with water, dried in the air, and recrystallized from ethanol to give 6-(3,4-dimethoxyphenyl)-2-methyl-4-[N-methyl-N-(2,4,6-trimethylphenyl)amino]pyrimidine (0.58 g).

mp: 124°–125° C.
IR (Nujol): 1580 cm$^{-1}$.
NMR (CDCl$_3$, δ): 7.51 (1H, d, J=2 Hz), 7.15 (1H, dd, J=2 Hz, 8 Hz), 6.95 (2H, s), 6.78 (1H, d, J=8 Hz), 5.93 (1H, s), 3.91 (3H, s), 3.84 (3H, s), 3.36 (3H, s), 2.65 (3H, s), 2.32 (3H, s), 2.07 (6H, s).

EXAMPLE 21

The following compounds were prepared according to the similar manner to that of Example 20.

(1)
6-(3,4-Dimethoxyphenyl)-4-[N-methyl-N-(2,4,6-trimethylphenyl)amino]pyrimidine mp: 124°–126° C.
IR (Nujol): 1585, 1520 cm$^{-1}$.
NMR (CDCl$_3$, δ): 8.74 (1H, s), 7.55 (1H, d, J=2 Hz), 7.16 (1H, dd, J=2 Hz), 6.97 (2H, s), 6.79 (1H, d, J=8 Hz), 6.12 (1H, s), 3.91 (3H, s), 3.86 (3H, s), 3.37 (3H, s), 2.34 (3H, s), 2.08 (6H, s).

(2)
6-(3,4-Dimethoxyphenyl)-2,5-dimethyl-4-[N-methyl-N-(2,4,6-trimethylphenyl)amino]pyrimidine mp: 148°–149° C.
IR (Nujol): 1550, 1525 cm$^{-1}$.
NMR (CDCl$_3$, δ): 7.1–6.8 (5H, m), 3.87 (6H, s), 3.34 (3H, s), 2.61 (3H, s), 2.29 (3H, s), 2.10 (6H, s), 1.30 (3H, s).

EXAMPLE 22

To a solution of 2-chloro-3,4-dihydro-6-(3,4-dimethoxyphenyl)-3-methyl-4-(2,4,6-trimethylphenylimino)pyrimidine (5.0 g) in tetrahydrofuran (50 ml) was bubbled ammonia gas to saturated at 0° C. The solution was sealed, and heated at 120° C. for 13 hours. The resulting suspension was chromatographed on silica gel, eluting with chloroform-methanol (95:5 v/v-90:10 v/v), to give 2-amino-3,4-dihydro-6-(3,4-dimethoxyphenyl)-3-methyl-4-(2,4,6-trimethylphenylimino)pyrimidine (2.64 g).

mp: 192°–195° C.
IR (Nujol): 1630, 1600 cm$^{-1}$.
NMR (CDCl$_3$, δ): 7.5–6.7 (5H, m), 5.74 (1H, s), 4.6 (2H, br s), 3.88 (6H, s), 3.80 (3H, s), 2.28 (3H, s), 2.07 (6H, s).

EXAMPLE 23

To a suspension of 2-chloro-3,4-dihydro-6-(3,4-dimethoxyphenyl)-3-methyl-4-(2,4,6-trimethylphenylimino)pyrimidine (2.08 g) in ethanol (20 ml) was added 1,2,3,6-tetrahydropyridine (1.38 ml), and refluxed for 1.5 hours. The resulting precipitates were collected, dissolved in chloroform, washed with aqueous sodium bicarbonate solution, and dried over magnesium sulfate. After evaporated, the residue was triturated with diisopropyl ether to give 3,4-dihydro-6-(3,4-dimethoxyphenyl)-3-methyl-2-(1,2,3,6-tetrahydropyridin-1-yl)-4-(2,4,6-trimethylphenylimino)pyrimidine (1.95 g).

mp: 161°–163° C.
IR (Nujol): 1640 cm$^{-1}$.
NMR (CDCl$_3$, δ): 7.45 (1H, d, J=2 Hz), 7.26 (1H, dd, J=2, 7 Hz), 6.83 (2H, s), 6.76 (1H, d, J=7 Hz), 5.82 (3H, s), 3.84 (6H, s), 3.82 (2H, s), 3.63 (3H, s), 3.3–3.6 (2H, m), 2.2–2.6 (2H, br s), 2.26 (3H, s), 2.02 (6H, s).

EXAMPLE 24

To a suspension of 3,4-dihydro-6-(3,4-dimethoxyphenyl)-3-methyl-4-(2,4,6-trimethylphenylimino)pyrimidine (2.0 g) in a mixture of ethanol (10 ml) and water (10 ml) was added sodium borohydride (1.04 g), and the mixture was stirred under reflux for 1.5 hours. After removal of the organic solvent, the mixture was suspended in water, and extracted with ethyl acetate. The organic layer was dried over magnesium sulfate, evaporated, and triturated in ethanol, to give 6-(3,4-dimethoxyphenyl)-3-methyl-1,2,3,4-tetrahydro-4-(2,4,6-trimethylphenylimino)pyrimidine (1.18 g).

mp: 165°–166° C.
IR (Nujol): 1620, 1605, 1590 cm$^{-1}$.
NMR (DMSO-d$_6$, δ): 7.2–6.7 (6H, m), 4.63 (1H, s), 4.38 (2H, s), 3.74 (6H, s), 2.92 (3H, s), 2.18 (3H, s), 1.95 (6H, s).

EXAMPLE 25

The following compounds were prepared according to a similar manner to that of Example 24.

(1)
1-Acetyl-6-(3,4-dimethoxyphenyl)-3-methyl-1,2,3,4-tetrahydro-4-(2,4,6-trimethylphenylimino)pyrimidine mp: 173°–175° C.
IR (Nujol): 1685, 1630 cm$^{-1}$.

(2)
6-(3,4-Dimethoxyphenyl)-2,3-dimethyl-1,2,3,4-tetrahydro-4-(2,4,6-trimethylphenylimino)pyrimidine was obtained by using lithium aluminum hydride in tetrahydrofuran instead of sodium borohydride.

mp: 141°–146° C.
IR (Nujol): 1620, 1590 cm$^{-1}$.
NMR (DMSO-d$_6$, δ): 7.1–6.7 (5H, m), 4.72 (1H, q, J=6 Hz), 4.47 (1H, s), 3.76 (6H, s), 2.93 (3H, s), 2.18 (3H, s), 1.97 (6H, s), 1.38 (3H, d, J=6 Hz).

EXAMPLE 26

To a solution of 6-(3,4-dimethoxyphenyl)-3-methyl-1,2,3,4-tetrahydro-4-(2,4,6-trimethylphenylimino)pyrimidine (0.5 g) in pyridine (5 ml) was added acetic anhydride (1.0 ml), and the mixture was stirred at ambient temperature for 2.5 hours. The mixture was poured into water (150 ml) and extracted with chloroform. The organic layer was washed with brine, dried over sodium sulfate, and evaporated. The residue was chromatographed on silica gel eluting with chloroform to give 1-acetyl-6-(3,4-dimethoxyphenyl)-3-methyl-1,2,3,4-tetrahydro-4-(2,4,6-trimethylphenylimino)pyrimidine (0.22 g).

mp: 173°-175° C.

IR (Nujol): 1685, 1630 cm$^{-1}$.

NMR (CDCl$_3$, δ): 7.0–6.7 (5H, m), 5.47 (1H, s), 5.07 (2H, s), 3.87 (3H, s), 3.81 (3H, s), 3.18 (3H, s), 2.26 (3H, s), 2.04 (6H, s), 1.77 (3H, s).

EXAMPLE 27

To a solution of 6-(3,4-dimethoxyphenyl)-2-methyl-4-(1-piperazinyl)pyrimidine (0.8 g) in chloroform (10 ml) were added triethylamine (0.39 ml) and 2,4-dichloro-5-sulfamoylbenzoyl chloride (0.74 g), and the mixture was stirred at ambient temperature for 20 hours. The reaction mixture was washed with water, dried over magnesium sulfate, and evaporated. The obtained mixture was chromatographed on silica gel eluting with chloroform-methanol mixture (49:1 v/v), to give 4-[4-(2,4-dichloro-5-sulfamoylbenzoyl)piperazin-1-yl]-6-(3,4-dimethoxyphenyl)-2-methylpyrimidine (1.03 g).

mp: 150°-160° C.

IR (Nujol): 1640, 1580 cm$^{-1}$.

NMR (CDCl$_3$, δ): 8.02 (1H, s), 7.7–7.4 (3H, m), 6.91 (1H, d, J=8 Hz), 6.67 (1H, s), 3.96 (3H, s), 3.92 (3H, s), 3.1–4.0 (8H, m), 2.57 (3H, s).

EXAMPLE 28

The solution of 3,4-dihydro-6-(3,4-dimethoxyphenyl)-3-methyl-4-(2,4,6-trimethylphenylimino)pyrimidine (3.0 g) in 1N hydrochloric acid (20 ml) was evaporated. The residue was ice-cooled, and crystallized. The crystals were filtered and dried to give 3,4-dihydro-6-(3,4-dimethoxyphenyl)-3-methyl-4-(2,4,6-trimethylphenylimino)pyrimidine hydrochloride (2.85 g).

mp: 165°-173° C.

IR (Nujol): 1630, 1580 cm$^{-1}$.

NMR (DMSO-d$_6$, δ): 11.13 (1H, br s), 9.13 (1H, s), 7.58 (1H, d, J=2 Hz), 7.42 (1H, dd, J=8 Hz), J=4 Hz), 7.12 (2H, s), 7.08 (1H, d, J=8 Hz), 6.77 (1H, s), 4.11 (3H, s), 3.81 (6H, s), 2.33 (3H, s), 2.19 (6H, s).

EXAMPLE 29

The following compound was prepared according to a similar manner to that of Example 28.

(1)

4,5-Dihydro-7-(3,4-dimethoxyphenyl)-4-methyl-5-(2,4,6-trimethylphenylimino)tetrazolo[1,5-a]-pyrimidine hydrochloride mp: 221° C. (dec.).

IR (Nujol): 1635, 1595, 2380 cm$^{-1}$.

NMR (DMSO-d$_6$, δ): 7.6–6.9 (5H, m), 6.19 and 5.80 (each s, total 1H), 4.20 and 3.95 (each s, total 3H), 3.82 and 3.76 (each s, total 6H), 2.32 and 2.25 (each s, total 3H), 2.16 and 2.08 (each s, total 6H).

EXAMPLE 30

To a solution of 2,4,6-trimethylphenol (1.03 g) in N,N-dimethylformamide (20 ml) was added sodium hydride (60% in oil, 0.30 g), and stirred at ambient temperature for 5 minutes. To the solution was added 4-chloro-6-(3,4-dimethoxyphenyl)-2-methylpyrimidine (2.0 g), and the mixture was stirred at ambient temperature for 18 hours. The solution was poured into water (300 ml), and extracted with ethyl acetate. The organic layer was washed with brine, dried over sodium sulfate and evaporated. The residue was chromatographed on silica gel eluting with chloroform to give 6-(3,4-dimethoxyphenyl)-2-methyl-4-(2,4,6-trimethylphenoxy)pyrimidine (1.96 g).

mp: 122°-125° C.

IR (Nujol): 1580 cm$^{-1}$.

NMR (CDCl$_3$, δ): 7.68 (1H, d, J=2 Hz), 7.50 (1H, dd, J=2 Hz, J=8 Hz), 6.93 (2H, s), 6.90 (1H, d, J=8 Hz), 6.74 (1H, s), 3.97 (3H, s), 3.93 (3H, s), 2.64 (3H, s), 2.33 (3H, s), 2.11 (6H, s).

EXAMPLE 31

The following compound was prepared according to a similar manner to those of Examples 16 and 18. 6-(3,4-Dimethoxyphenyl)-4-(4-aminophenylamino)-2-methylpyrimidine.

mp: 216°-217° C.

IR (Nujol): 1600, 1580 cm$^{-1}$.

NMR (CDCl$_3$-CD$_3$OD, δ): 7.52 (1H, d, J=2 Hz), 7.36 (1H, dd, J=2 Hz, 8 Hz), 7.09 (2H, d, J=9 Hz), 6.86 (1H, d, J=8 Hz), 6.70 (2H, d, J=9 Hz), 6.68 (1H, s), 3.93 (3H, s), 3.88 (3H, s), 2.57 (3H, s).

EXAMPLE 32

The following compounds were prepared according to the similar manner to that of Example 26 or 27.

(1)

1-Acetyl-6-(3,4-dimethoxyphenyl)-2,3-dimethyl-1,2,3,4-tetrahydro-4-(2,4,6-trimethylphenylimino)pyrimidine (0.15 g) was obtained by reacting corresponding 1-unsubstituted compound (0.41 g) with acetic anhydride (2 ml).

mp: 87°-89° C.

IR (Nujol): 1690, 1630 cm$^{-1}$.

NMR (CDCl$_3$, δ): 6.80 (4H, br s), 6.66 (1H, br s), 6.10 (1H, q, J=6 Hz), 5.41 (1H, s), 3.84 (3H, s), 3.79 (3H, s), 3.09 (3H, s), 2.23 (3H, s), 2.00 (6H, s), 1.70 (3H, s), 1.39 (3H, d, J=6 Hz).

(2)

6-(3,4-Dimethoxyphenyl)-3-methyl-1-propionyl-1,2,3,4-tetrahydro-4-(2,4,6-trimethylphenylimino)pyrimidine (0.3 g) was obtained by reacting corresponding 1-unsubstituted compound (0.64 g) with propionyl chloride (0.8 ml).

mp: 178°-180° C.

IR (Nujol): 1690, 1645, 1630 cm$^{-1}$.

NMR (CDCl$_3$, δ): 7.0–6.6 (5H, m), 5.43 (1H, s), 5.04 (2H, s), 3.86 (3H, s), 3.80 (3H, s), 3.15 (3H, s), 2.24 (3H, s), 2.03 (6H, s), 1.92 (2H, q, J=7 Hz), 0.94 (3H, t, J=7 Hz).

EXAMPLE 33

To a solution of 4-(4-aminophenylamino)-6-(3,4-dimethoxyphenyl)-2-methylpyrimidine (1.0 g) in 1,2-dichloroethane (20 ml) were added methanesulfonyl chloride (0.28 ml) and triethylamine (0.83 ml) and the mixture was refluxed for 3 hours. After cooled, chloroform (50 ml) was added thereto, and washed with water. The solution was dried over magnesium sulfate, evaporated, and chromatographed on silica gel eluting with chloroform to give 6-(3,4-dimethoxyphenyl)-4-(4-mesylaminophenylamino)-2-methylpyrimidine (0.45 g).

mp: 180°–185° C.
IR (Nujol): 1610, 1590 cm$^{-1}$.
NMR (CDCl$_3$-MeOHd$_4$, δ): 7.7–6.85 (7H, m), 6.83 (1H, s), 3.96 (3H, s), 3.93 (3H, s), 2.99 (3H, s), 2.62 (3H, s).

EXAMPLE 34

The following compound was prepared according to the similar manner to that of Example 33.

(1)
3,4-Dihydro-6-(3,4-dimethoxyphenyl)-2-mesylamino-3-methyl-4-(2,4,6-trimethylphenylimino)pyrimidine mp: 260°–262° C.
IR (Nujol): 1595, 1570 cm$^{-1}$.
NMR (DMSO-d$_6$, δ): 9.35 (1H, br s), 7.60 (1H, br d, J=2 Hz), 7.4–6.9 (4H, m), 5.63 (1H, s), 3.80 (3H, s), 3.77 (3H, s), 3.30 (3H, s), 3.12 (3H, s), 2.34 (3H, s), 2.19 (6H, s).

EXAMPLE 35

To a solution of 6-(3,4-dimethoxyphenyl)-3-methyl-1,2,3,4-tetrahydro-4-(2,4,6-trimethylphenylimino)pyrimidine (1.0 g) in pyridine (10 ml) was added methyl isocyanate (0.18 ml), and the mixture was stirred at ambient temperature for 3 hours. Then the mixture was poured into water (150 ml), and the resultant precipitates were collected. The precipitates were washed with water, and dried to give 6-(3,4-dimethoxyphenyl)-3-methyl-1-(N-methylcarbamoyl)-1,2,3,4-tetrahydro-4-(2,4,6-trimethylphenylimino)pyrimidine (0.99 g).

mp: 184°–187° C.
IR (Nujol): 1675, 1625, 1600 cm$^{-1}$.
NMR (CDCl$_3$, δ): 6.9–6.7 (5H, m), 5.43 (1H, s), 5.03 (2H, s), 4.32 (1H, br d, J=5 Hz), 3.86 (3H, s), 3.81 (3H, s), 3.13 (3H, s), 2.62 (3H, d, J=5 Hz), 2.24 (3H, s), 2.02 (6H, s).

What is claimed is:
1. A pyrimidine compound of the formula:

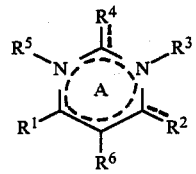

wherein
$R^1$ is hydrogen, di(lower)alkoxyphenyl or pyridyl;
$R^2$ is (a) =N—$R_a^2$ or (b)

or —O—$R_a^2$ in which $R_a^2$ is 2,4,6-tri(lower)alkylphenyl, aminophenyl or acylaminophenyl and $R_b^2$ is lower alkyl,
$R^3$ is hydrogen, lower alkyl or no significance;
$R^4$ is (a) imino optionally substituted with lower alkyl, phenyl or benzyl or (b) lower alkyl, hydrogen, halogen, lower alkylthio, amino optionally substituted with one or two substitutent(s) selected from lower alkyl, phenyl, benzyl and acyl, —N⌒C⌒ or hydrazino optionally substituted with one acyl, in which —N⌒C⌒ is teteahydropyridin-1-yl or 1-piperazinyl optionally substituted with one acyl,
$R^5$ is hydrogen, lower alkyl, lower alkanoyl optionally substituted with one lower alkylamino or no significance;
$R^6$ is hydrogen, lower alkyl, or di(lower)alkoxyphenyl; the ═ bond represents single bond or double bond; and the dotted line in the ring A represents one, two or three additional C—C and/or C—N bond(s) in the ring system, provided that $R^1$ and $R^6$ are not both hydrogen; and pharmaceutically acceptable salt thereof.

2. A compound as claimed in claim 1, which is a compound of the formula:

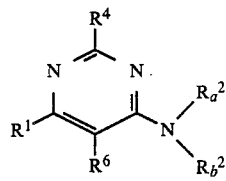

wherein $R^1$, $R_a^2$, $R_b^2$, $R^4$ and $R^6$ are each as defined in claim 1,

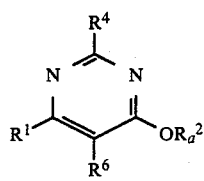

wherein $R^1$, $R_a^2$, $R^4$ and $R^6$ are each as defined in claim 1,

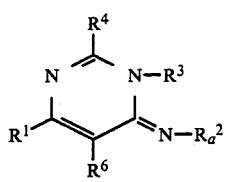

wherein $R^1$, $R_a^2$, $R^4$ and $R^6$ are each defined in claim 1,

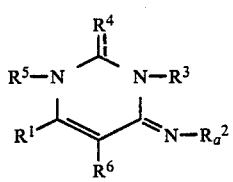

wherein $R^1$, $R_a^2$, $R^3$, $R^4$, $R^5$, $R^6$ and═are each as defined in claim 1, or

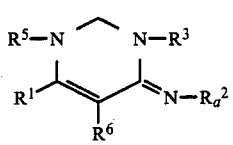

wherein $R^1$, $R_a^2$, $R^3$, $R^5$ and $R^6$ are each as defined in claim 1 and pharmaceutically acceptable salt thereof.

3. A compound as claimed in claim 1, wherein $R^1$ is di(lower)alkoxyphenyl.

4. A compound as claimed in claim 3, wherein $R^6$ is hydrogen.

5. A compound as claimed in claim 4, wherein $R^2$ is $=N-R_a^2$ in which $R_a^2$ is the same as claim 1.

6. A compound as claimed in claim 5, wherein $R_a^2$ is 2,4,6-tri(lower)alkylphenyl.

7. A compound as claimed in claim 6, wherein $R^3$ is lower alkyl.

8. A compound as claimed in claim 7, wherein $R^4$ is halogen.

9. A compound as claimed in claim 8, which is 2-chloro-3,4-dihydro-6-(3,4-dimethoxyphenyl)-3-methyl-4-(2,4,6-trimethylphenylimino)pyrimidine.

10. A compound as claimed in claim 7, wherein $R^4$ is hydrogen.

11. A compound as claimed in claim 10, which is 3,4-dihydro-6-(3,4-dimethoxyphenyl)-3-methyl-4-(2,4,6-trimethylphenylimino)pyrimidine.

12. A compound as claimed in claim 7, wherein $R^4$ is lower alkyl.

13. A compound as claimed in claim 12, which is 3,4-dihydro-6-(3,4-dimethoxyphenyl)-2,3-dimethyl-4-(2,4,6-trimethylphenylimino)pyrimidine.

14. A compound as claimed in claim 12, which is 3,4-dihydro-6-(3,4-dimethoxyphenyl)-3-ethyl-2-methyl-4-(2,4,6-trimethylphenylimino)pyrimidine.

15. A compound as claimed in claim 4, wherein

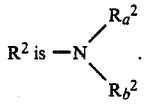

16. A compound as claimed in claim 15, wherein $R^4$ is lower alkyl.

17. A cardiotonic, antihypertensive, cerebrovascular vasodilative and anti-platelet aggregation pharmaceutical composition comprising an effective "cardiotonic, antihypertensive, cerebrovascular vasodilative or anti-platelet aggregation" amount of a compound of claim 1 in association with a pharmaceutically acceptable, substantially non-toxic carrier or excipient.

18. A pyrimidine compound of the formula:

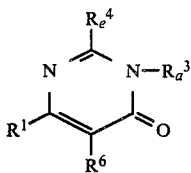

wherein
$R^1$ is hydrogen, di(lower)alkoxyphenyl or pyridyl;
$R^6$ is hydrogen, lower alkyl or di(lower)alkoxyphenyl;
$R_a^3$ is lower alkyl;
$R_e^4$ is hydrogen or lower alkyl; and pharmaceutically acceptable salt thereof.

* * * * *